(12) United States Patent
Lee-Sepsick et al.

(10) Patent No.: US 8,048,086 B2
(45) Date of Patent: *Nov. 1, 2011

(54) METHODS AND DEVICES FOR CONDUIT OCCLUSION

(75) Inventors: Kathy Lee-Sepsick, Suwanee, GA (US);
Lani L. L. Paxton, Decatur, GA (US);
Jeffrey A. Marcus, Atlanta, GA (US);
Stephen N. Williams, Atlanta, GA (US)

(73) Assignee: Femasys Inc., Suwanee, GA (US)

( * ) Notice: Subject to any disclaimer, the term of this patent is extended or adjusted under 35 U.S.C. 154(b) by 1391 days.

This patent is subject to a terminal disclaimer.

(21) Appl. No.: 11/065,886

(22) Filed: Feb. 24, 2005

(65) Prior Publication Data

US 2005/0187561 A1 Aug. 25, 2005

Related U.S. Application Data

(60) Provisional application No. 60/547,491, filed on Feb. 25, 2004, provisional application No. 60/587,604, filed on Jul. 13, 2004.

(51) Int. Cl.
*A61F 11/00* (2006.01)
*A61K 9/00* (2006.01)
*A61K 9/14* (2006.01)

(52) U.S. Cl. ......... 606/108; 424/400; 424/423; 424/489

(58) Field of Classification Search .................. None
See application file for complete search history.

(56) References Cited

U.S. PATENT DOCUMENTS

| | | | |
|---|---|---|---|
| 1,892,803 A | 1/1933 | Lawshe | |
| 3,042,030 A | 7/1962 | Read | |
| 3,182,662 A | 5/1965 | Shirodkar | |
| 3,404,682 A | 10/1968 | Waldron | |
| 3,405,711 A | 10/1968 | Bakunin | |
| 3,422,813 A | 1/1969 | Braley et al. | |
| 3,463,141 A | 8/1969 | Mozolf | |
| 3,467,090 A | 9/1969 | Zollett | |
| 3,598,115 A | 8/1971 | Horne | |
| 3,645,258 A | 2/1972 | Massouras | |
| 3,675,642 A | 7/1972 | Lord | |
| 3,680,542 A | 8/1972 | Cimber | |
| 3,687,129 A | 8/1972 | Nuwayser | |
| 3,768,102 A | 10/1973 | Kwan-Gett et al. | |
| 3,774,600 A | 11/1973 | Cognat | |
| 3,803,308 A | 4/1974 | Zipper | |
| 3,805,767 A | 4/1974 | Erb | |
| 3,822,702 A * | 7/1974 | Bolduc et al. | 128/831 |
| 3,855,996 A | 12/1974 | Bolduc | |
| 3,856,016 A | 12/1974 | Davis | |
| 3,858,571 A | 1/1975 | Rudolph | |
| 3,858,586 A | 1/1975 | Lessen | |
| 3,871,374 A | 3/1975 | Bolduc et al. | |
| 3,875,939 A | 4/1975 | Bolduc et al. | |
| 3,882,854 A | 5/1975 | Hulka et al. | |
| 3,918,431 A | 11/1975 | Sinnreich | |
| 3,948,259 A | 4/1976 | Bolduc et al. | |
| 3,954,108 A | 5/1976 | Davis | |
| 3,967,625 A | 7/1976 | Yoon | |
| 3,972,331 A | 8/1976 | Bolduc et al. | |
| 3,973,560 A | 8/1976 | Emmett | |
| RE29,207 E | 5/1977 | Bolduc et al. | |
| RE29,345 E | 8/1977 | Erb | |
| 4,109,654 A | 8/1978 | Bolduc et al. | |
| 4,119,098 A | 10/1978 | Bolduc et al. | |
| 4,126,134 A | 11/1978 | Bolduc et al. | |
| 4,135,495 A | 1/1979 | Borgen | |
| 4,136,695 A | 1/1979 | Dafoe | |
| 4,158,050 A | 6/1979 | Zipper | |
| 4,160,446 A | 7/1979 | Barrington | |
| 4,181,725 A | 1/1980 | Voorhees et al. | |
| 4,182,328 A | 1/1980 | Bolduc et al. | |
| 4,185,618 A | 1/1980 | Corey | |
| 4,207,891 A | 6/1980 | Bolduc | |
| 4,226,239 A | 10/1980 | Polk et al. | |
| 4,230,116 A | 10/1980 | Watson | |
| 4,245,623 A | 1/1981 | Erb | |
| 4,267,839 A | 5/1981 | Laufe et al. | |
| 4,359,454 A | 11/1982 | Hoffman | |
| 4,365,621 A | 12/1982 | Brundin | |
| 4,374,523 A | 2/1983 | Yoon | |
| 4,380,238 A | 4/1983 | Colucci et al. | |

(Continued)

FOREIGN PATENT DOCUMENTS

DE 25 37 620 2/1977
(Continued)

OTHER PUBLICATIONS

Basu, et al., Ann. Thorac. Surg., 60, 1995, pp. 1255-1262.*

(Continued)

*Primary Examiner* — Robert A Wax
*Assistant Examiner* — William Craigo
(74) *Attorney, Agent, or Firm* — Ballard Spahr LLP

(57) ABSTRACT

The present invention comprises systems, methods and devices for the delivery of compositions for occluding or of means for opening conduits. The implantable occlusive material may be delivered pre-formed or in situ cured and, may be a resorbable material that supports tissue ingrowth that eventually replaces the material leaving little or no original material in place. The delivery system is positioned to allow for placement of the occlusive material into the body conduit. Use of delivery systems, methods and devices for re-opening an occluded body conduit are also included.

30 Claims, 6 Drawing Sheets

U.S. PATENT DOCUMENTS

| | | |
|---|---|---|
| 4,416,660 A | 11/1983 | Dafoe |
| 4,485,814 A | 12/1984 | Yoon |
| 4,489,725 A | 12/1984 | Casey et al. |
| 4,509,504 A | 4/1985 | Brundin |
| 4,523,590 A | 6/1985 | Roth et al. |
| 4,537,186 A | 8/1985 | Verschoof et al. |
| 4,547,188 A | 10/1985 | Bolduc |
| 4,548,201 A | 10/1985 | Yoon |
| 4,579,110 A | 4/1986 | Hamou |
| 4,595,000 A | 6/1986 | Hamou |
| 4,601,698 A | 7/1986 | Moulding, Jr. |
| 4,606,336 A | 8/1986 | Zeluff |
| 4,611,602 A | 9/1986 | Bolduc |
| 4,631,188 A | 12/1986 | Stoy et al. |
| 4,637,818 A | 1/1987 | Johnson et al. |
| 4,664,112 A | 5/1987 | Kensey et al. |
| 4,679,558 A | 7/1987 | Kensey et al. |
| 4,681,106 A | 7/1987 | Kensey et al. |
| 4,700,701 A | 10/1987 | Montaldi |
| 4,700,705 A | 10/1987 | Kensey et al. |
| 4,713,235 A | 12/1987 | Krall |
| 4,731,052 A | 3/1988 | Seitz, Jr. |
| 4,788,966 A | 12/1988 | Yoon |
| 4,794,927 A | 1/1989 | Yoon |
| 4,795,438 A | 1/1989 | Kensey et al. |
| 4,804,691 A | 2/1989 | English et al. |
| 4,808,399 A | 2/1989 | Rypácek et al. |
| 4,824,434 A | 4/1989 | Seitz, Jr. |
| 4,834,091 A | 5/1989 | Ott |
| 4,847,065 A | 7/1989 | Akimova et al. |
| 4,869,268 A | 9/1989 | Yoon |
| 4,932,422 A | 6/1990 | Ragheb |
| 4,937,254 A | 6/1990 | Sheffield et al. |
| 4,938,763 A | 7/1990 | Dunn et al. |
| 4,983,177 A | 1/1991 | Wolf |
| 5,026,379 A | 6/1991 | Yoon |
| 5,065,751 A | 11/1991 | Wolf |
| 5,095,917 A | 3/1992 | Vancaillie |
| 5,147,353 A | 9/1992 | Everett |
| 5,193,554 A | 3/1993 | McQuilkin |
| 5,211,627 A * | 5/1993 | William .................. 604/82 |
| 5,217,030 A | 6/1993 | Yoon |
| 5,217,473 A | 6/1993 | Yoon |
| 5,226,908 A | 7/1993 | Yoon |
| 5,273,527 A | 12/1993 | Schatz et al. |
| 5,278,201 A | 1/1994 | Dunn et al. |
| 5,278,202 A | 1/1994 | Dunn et al. |
| 5,324,519 A | 6/1994 | Dunn et al. |
| 5,328,687 A | 7/1994 | Leung et al. |
| 5,334,209 A | 8/1994 | Yoon |
| 5,340,849 A | 8/1994 | Dunn et al. |
| 5,350,798 A | 9/1994 | Linden et al. |
| 5,352,436 A | 10/1994 | Wheatley et al. |
| 5,364,345 A | 11/1994 | Lowery et al. |
| 5,372,584 A * | 12/1994 | Zink et al. .................. 604/515 |
| 5,374,247 A | 12/1994 | Lowery et al. |
| 5,389,089 A | 2/1995 | Bauer et al. |
| 5,391,146 A | 2/1995 | That et al. |
| 5,464,395 A | 11/1995 | Faxon et al. |
| 5,469,867 A | 11/1995 | Schmitt |
| 5,474,089 A | 12/1995 | Waynant |
| 5,478,837 A | 12/1995 | Rodgers et al. |
| 5,487,390 A | 1/1996 | Cohen et al. |
| 5,487,897 A | 1/1996 | Polson et al. |
| 5,551,443 A | 9/1996 | Sepetka et al. |
| 5,562,099 A | 10/1996 | Cohen et al. |
| 5,575,802 A | 11/1996 | McQuilkin et al. |
| 5,599,552 A | 2/1997 | Dunn et al. |
| 5,601,600 A | 2/1997 | Ton |
| 5,612,052 A | 3/1997 | Shalaby |
| 5,632,727 A | 5/1997 | Tipton et al. |
| 5,632,753 A | 5/1997 | Loeser |
| 5,634,877 A | 6/1997 | Salama |
| 5,681,873 A | 10/1997 | Norton et al. |
| 5,701,899 A * | 12/1997 | Porter .................. 600/458 |
| 5,702,716 A | 12/1997 | Dunn et al. |
| 5,702,717 A | 12/1997 | Cha et al. |
| 5,704,899 A | 1/1998 | Milo |
| 5,714,159 A | 2/1998 | Shalaby |
| 5,716,321 A | 2/1998 | Kerin et al. |
| 5,725,777 A | 3/1998 | Taylor |
| 5,733,950 A | 3/1998 | Dunn et al. |
| 5,736,152 A | 4/1998 | Dunn |
| 5,739,176 A | 4/1998 | Dunn et al. |
| 5,744,153 A | 4/1998 | Yewey et al. |
| 5,746,769 A | 5/1998 | Ton et al. |
| 5,747,058 A | 5/1998 | Tipton et al. |
| 5,752,974 A | 5/1998 | Rhee et al. |
| 5,759,563 A | 6/1998 | Yewey et al. |
| 5,780,044 A | 7/1998 | Yewey et al. |
| 5,788,716 A | 8/1998 | Kobren et al. |
| 5,792,469 A | 8/1998 | Tipton et al. |
| 5,795,288 A | 8/1998 | Cohen et al. |
| 5,795,331 A | 8/1998 | Cragg et al. |
| 5,807,239 A | 9/1998 | DiBernardo |
| 5,826,584 A | 10/1998 | Schmitt |
| 5,830,228 A | 11/1998 | Knapp et al. |
| 5,843,121 A | 12/1998 | Yoon |
| 5,846,255 A | 12/1998 | Casey |
| 5,866,554 A | 2/1999 | Shalaby et al. |
| 5,873,815 A | 2/1999 | Kerin et al. |
| 5,885,601 A | 3/1999 | Sokal |
| 5,888,533 A | 3/1999 | Dunn |
| 5,891,192 A | 4/1999 | Murayama et al. |
| 5,891,457 A | 4/1999 | Neuwirth |
| 5,894,022 A | 4/1999 | Ji et al. |
| 5,919,434 A * | 7/1999 | Dugstad et al. .............. 424/9.52 |
| 5,935,056 A | 8/1999 | Kerin et al. |
| 5,935,098 A | 8/1999 | Blaisdell et al. |
| 5,935,137 A | 8/1999 | Saadat et al. |
| 5,947,958 A | 9/1999 | Woodard et al. |
| 5,947,977 A | 9/1999 | Slepian et al. |
| 5,954,715 A | 9/1999 | Harrington et al. |
| 5,955,143 A | 9/1999 | Wheatley et al. |
| 5,962,006 A | 10/1999 | Southard et al. |
| 5,968,542 A | 10/1999 | Tipton |
| 5,972,002 A | 10/1999 | Bark et al. |
| 5,979,446 A | 11/1999 | Loy |
| 5,989,580 A * | 11/1999 | Wallace et al. .............. 424/433 |
| 5,990,194 A | 11/1999 | Dunn et al. |
| 6,010,714 A | 1/2000 | Leung et al. |
| 6,019,757 A | 2/2000 | Scheldrup |
| 6,026,331 A | 2/2000 | Feldberg et al. |
| 6,037,331 A | 3/2000 | Shalaby et al. |
| 6,042,590 A | 3/2000 | Sporri et al. |
| 6,066,139 A | 5/2000 | Ryan et al. |
| 6,068,626 A | 5/2000 | Harrington et al. |
| 6,071,283 A | 6/2000 | Nardella et al. |
| 6,080,129 A | 6/2000 | Blaisdell |
| 6,080,152 A | 6/2000 | Nardella et al. |
| 6,096,052 A | 8/2000 | Callister et al. |
| 6,103,254 A | 8/2000 | Wallace et al. |
| 6,112,747 A | 9/2000 | Jones et al. |
| 6,113,614 A | 9/2000 | Mears |
| 6,120,789 A | 9/2000 | Dunn |
| 6,130,200 A | 10/2000 | Brodbeck et al. |
| 6,143,352 A | 11/2000 | Clark et al. |
| 6,145,505 A | 11/2000 | Nikolchev et al. |
| 6,152,943 A | 11/2000 | Sawhney |
| 6,165,492 A | 12/2000 | Neuwirth |
| 6,174,919 B1 | 1/2001 | Hickey |
| 6,176,240 B1 | 1/2001 | Nikolchev et al. |
| 6,179,832 B1 | 1/2001 | Jones et al. |
| 6,187,346 B1 | 2/2001 | Neuwirth |
| 6,196,966 B1 | 3/2001 | Kerin et al. |
| 6,197,351 B1 | 3/2001 | Neuwirth |
| 6,245,090 B1 | 6/2001 | Gilson et al. |
| 6,258,084 B1 | 7/2001 | Goldman et al. |
| 6,297,337 B1 | 10/2001 | Marchant et al. |
| 6,299,631 B1 | 10/2001 | Shalaby |
| 6,306,243 B1 | 10/2001 | Clark et al. |
| 6,309,384 B1 | 10/2001 | Harrington et al. |
| 6,327,505 B1 | 12/2001 | Medhkour et al. |
| 6,346,102 B1 | 2/2002 | Harrington et al. |
| 6,357,443 B1 | 3/2002 | Loy |
| 6,371,975 B2 | 4/2002 | Cruise et al. |
| 6,378,524 B1 | 4/2002 | Jones |

| | | |
|---|---|---|
| 6,379,373 B1 | 4/2002 | Sawhney et al. |
| 6,395,293 B2 | 5/2002 | Polson et al. |
| 6,401,719 B1 | 6/2002 | Farley et al. |
| 6,413,536 B1 | 7/2002 | Gibson et al. |
| 6,413,539 B1 | 7/2002 | Shalaby |
| 6,432,116 B1 | 8/2002 | Callister et al. |
| 6,433,096 B1 | 8/2002 | Hickey et al. |
| 6,455,064 B1 | 9/2002 | Narang et al. |
| 6,458,147 B1 | 10/2002 | Cruise et al. |
| 6,461,631 B1 | 10/2002 | Dunn et al. |
| 6,465,001 B1 | 10/2002 | Hubbell et al. |
| 6,476,069 B2 | 11/2002 | Krall et al. |
| 6,476,070 B2 | 11/2002 | Krall et al. |
| 6,485,486 B1 | 11/2002 | Trembly et al. |
| RE37,950 E | 12/2002 | Dunn et al. |
| 6,493,589 B1 | 12/2002 | Medhkour et al. |
| 6,514,534 B1 | 2/2003 | Sawhney |
| 6,514,535 B2 | 2/2003 | Marchant |
| 6,526,979 B1 | 3/2003 | Nikolchev et al. |
| 6,528,080 B2 | 3/2003 | Dunn et al. |
| 6,538,026 B1 | 3/2003 | Krall et al. |
| 6,539,265 B2 | 3/2003 | Medhkour et al. |
| 6,550,480 B2 | 4/2003 | Feldman et al. |
| 6,565,557 B1 | 5/2003 | Sporri et al. |
| 6,577,903 B1 | 6/2003 | Cronin et al. |
| 6,579,469 B1 | 6/2003 | Nicholson et al. |
| 6,599,299 B2 | 7/2003 | Schultz |
| 6,605,294 B2 | 8/2003 | Sawhney |
| 6,605,667 B1 | 8/2003 | Badejo et al. |
| 6,607,631 B1 | 8/2003 | Badejo et al. |
| 6,610,033 B1 | 8/2003 | Melanson et al. |
| 6,620,846 B1 | 9/2003 | Jonn et al. |
| 6,634,361 B1 | 10/2003 | Nikolchev et al. |
| 6,635,055 B1 | 10/2003 | Cronin |
| 6,663,607 B2 | 12/2003 | Slaikeu et al. |
| 6,676,971 B2 | 1/2004 | Goupil et al. |
| 6,679,266 B2 | 1/2004 | Nikolchev et al. |
| 6,682,526 B1 | 1/2004 | Jones et al. |
| 6,684,884 B2 | 2/2004 | Nikolchev et al. |
| 6,689,148 B2 | 2/2004 | Sawhney et al. |
| 6,699,940 B2 | 3/2004 | Shalaby |
| 6,703,047 B2 | 3/2004 | Sawhney et al. |
| 6,705,323 B1 | 3/2004 | Nikolchev et al. |
| 6,709,667 B1 | 3/2004 | Lowe et al. |
| 6,712,810 B2 | 3/2004 | Harrington et al. |
| 6,723,144 B2 | 4/2004 | Katagiri et al. |
| 6,723,781 B1 | 4/2004 | Frate et al. |
| 6,726,682 B2 | 4/2004 | Harrington et al. |
| 6,736,822 B2 | 5/2004 | McClellan et al. |
| 6,743,248 B2 | 6/2004 | Edwards et al. |
| 6,752,803 B2 | 6/2004 | Goldman et al. |
| 6,758,831 B2 * | 7/2004 | Ryan ............... 604/103.03 |
| 6,763,833 B1 | 7/2004 | Khera et al. |
| 6,780,182 B2 | 8/2004 | Bowman et al. |
| 2001/0016738 A1 | 8/2001 | Harrington et al. |
| 2001/0016739 A1 | 8/2001 | Goldman et al. |
| 2001/0023365 A1 | 9/2001 | Medhkour et al. |
| 2001/0041900 A1 | 11/2001 | Callister et al. |
| 2002/0013589 A1 | 1/2002 | Callister et al. |
| 2002/0020417 A1 | 2/2002 | Nikolchev et al. |
| 2002/0029051 A1 * | 3/2002 | Callister et al. ............ 606/157 |
| 2002/0035101 A1 | 3/2002 | Dey et al. |
| 2002/0072744 A1 | 6/2002 | Harrington et al. |
| 2002/0082636 A1 * | 6/2002 | Sawhney et al. ............ 606/193 |
| 2002/0106411 A1 | 8/2002 | Wironen et al. |
| 2002/0133140 A1 | 9/2002 | Moulis |
| 2002/0148476 A1 | 10/2002 | Farley et al. |
| 2002/0176893 A1 | 11/2002 | Wironen et al. |
| 2002/0177846 A1 | 11/2002 | Mulier et al. |
| 2002/0177855 A1 | 11/2002 | Greene, Jr. et al. |
| 2003/0015203 A1 | 1/2003 | Makower et al. |
| 2003/0029457 A1 | 2/2003 | Callister et al. |
| 2003/0051735 A1 | 3/2003 | Pavcnik et al. |
| 2003/0060800 A1 | 3/2003 | Ryan |
| 2003/0066533 A1 | 4/2003 | Loy |
| 2003/0108586 A1 | 6/2003 | Ramey |
| 2003/0134032 A1 | 7/2003 | Chaouk et al. |
| 2003/0158563 A1 | 8/2003 | McClellan et al. |
| 2003/0170173 A1 * | 9/2003 | Klaveness et al. .......... 424/1.11 |
| 2003/0171759 A1 | 9/2003 | Sadler et al. |
| 2003/0185896 A1 | 10/2003 | Buiser et al. |
| 2003/0194389 A1 | 10/2003 | Porter |
| 2003/0194390 A1 | 10/2003 | Krall et al. |
| 2003/0223956 A1 | 12/2003 | Goupil et al. |
| 2004/0002680 A1 | 1/2004 | Ackerman et al. |
| 2004/0079377 A1 | 4/2004 | Nikolchev et al. |
| 2004/0127918 A1 | 7/2004 | Nikolchev et al. |
| 2004/0159324 A1 | 8/2004 | Nikolchev et al. |
| 2004/0163650 A1 | 8/2004 | Lowe et al. |
| 2004/0204720 A1 | 10/2004 | Harrington et al. |
| 2004/0206358 A1 | 10/2004 | Nikolchev et al. |
| 2004/0211429 A1 | 10/2004 | Nikolchev et al. |
| 2004/0215215 A1 | 10/2004 | McClellan et al. |
| 2004/0258761 A1 | 12/2004 | Wheatley et al. |
| 2004/0258769 A1 | 12/2004 | Barker et al. |

FOREIGN PATENT DOCUMENTS

| | | |
|---|---|---|
| FR | 2 414 925 | 8/1979 |
| GB | 1470571 | 4/1997 |
| JP | 59-046500 | 3/1984 |
| JP | 2002-200176 | 7/2002 |
| WO | WO 81/00701 | 3/1981 |
| WO | WO 88/09648 | 12/1988 |
| WO | WO 93/14786 | 8/1993 |
| WO | WO 94/24944 | 11/1994 |
| WO | WO 94/28803 | 12/1994 |
| WO | WO 95/25490 | 9/1995 |
| WO | WO 97/12569 | 4/1997 |
| WO | WO 97/42987 | 11/1997 |
| WO | WO 97/49345 | 12/1997 |
| WO | WO 98/26737 | 6/1998 |
| WO | WO 98/31308 | 7/1998 |
| WO | WO 99/07297 | 2/1999 |
| WO | WO 99/47073 | 9/1999 |
| WO | WO 00/18469 | 4/2000 |
| WO | WO 00/24374 | 5/2000 |
| WO | WO 00/44323 | 8/2000 |
| WO | WO 00/54746 | 9/2000 |
| WO | WO 01/37760 | 5/2001 |
| WO | WO 02/39880 | 5/2002 |
| WO | WO 03/070085 | 8/2003 |
| WO | WO 2004/024237 | 3/2004 |
| WO | WO 2004/035022 | 4/2004 |
| WO | WO 2005/082299 | 9/2005 |

OTHER PUBLICATIONS

Saito, et al., Acta Bio, 3, 2007, pp. 89-94.*
Volpi, et al., Ultrasound Obstet. Gynecol., 7, 1996, pp. 43-48.*
Wilson, International Journal of Gynecology and Obstetrics, 51, 1995.*
Wilson, IJGynOB, 51, 1995.*
International Search Report issued Sep. 22, 2005 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant).
Written Opinion issued Sep. 22, 2005 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant).
International Preliminary Report on Patentability issued Aug. 30, 2006 for PCT Application No. PCT/US2005/006334 filed on Feb. 25, 2005, which published as WO/2005/082299 on Sep. 9, 2005 (Lee-Sepsick et al. listed as inventors and Femasys Inc. listed as Applicant).
First Office Action issued Nov. 30, 2007 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to First Office Action filed Jun. 16, 2008 for Chinese Application No. CN 200580006068.X, which claims priority to PCT/US2005/006334 filed on Feb. 25, 2005 (Lee-Sepsick et al. listed as inventors and Femasys Inc. listed as Applicant).
Second Office Action issued Dec. 12, 2008 for Chinese Application No. CN 200580006068.X, which claims priority to PCT/US2005/

006334 filed on Feb. 25, 2005 (Lee-Sepsick et al. listed as inventors and Femasys Inc. listed as Applicant).
Response to Second Office Action filed Apr. 24, 2009 for Chinese Application No. CN 200580006068.X, which claims priority to PCT/US2005/006334 filed on Feb. 25, 2005 (Lee-Sepsick et al. listed as inventors and Femasys Inc. listed as Applicant).
Third Office Action issued Jun. 24, 2010 for Chinese Application No. CN 200580006068.X, which claims priority to PCT/US2005/006334 filed on Feb. 25, 2005 (Lee-Sepsick et al. listed as inventors and Femasys Inc. listed as Applicant).
Response to Third Office Action filed Sep. 6, 2010 with Allowed Claims for Chinese Application No. CN 200580006068.X, which claims priority to PCT/US2005/006334 filed on Feb. 25, 2005 (Lee-Sepsick et al. listed as inventors and Femasys Inc. listed as Applicant).
Voluntary Amendments filed Mar. 1, 2010 for Canadian Application No. CA 2556747, which claims priority to PCT/US2005/006334 filed on Feb. 25, 2005 (Lee-Sepsick et al. listed as inventors and Femasys Inc. listed as Applicant).
Examination Report issued Apr. 19, 2011 for Canadian Application No. CA 2556747, which claims priority to PCT/US2005/006334 filed on Feb. 25, 2005 (Lee-Sepsick et al. listed as inventors and Femasys Inc. listed as Applicant).
Examination Report issued Apr. 21, 2010 for Indian Application No. 2536/KOLNP/2006, which claims priority to PCT/US2005/006334 filed on Feb. 25, 2005 (Lee-Sepsick et al. listed as inventors and Femasys Inc. listed as Applicant).
Response filed Apr. 5, 2011 for Indian Application No. 2536/KOLNP/2006, which claims priority to PCT/US2005/006334 filed on Feb. 25, 2005 (Lee-Sepsick et al. listed as inventors and Femasys Inc. listed as Applicant).
Response filed Apr. 13, 2011 for Indian Application No. 2536/KOLNP/2006, which claims priority to PCT/US2005/006334 filed on Feb. 25, 2005 (Lee-Sepsick et al. listed as inventors and Femasys Inc. listed as Applicant).
Office Action issued May 11, 2010 for Japanese Application No. JP2007-500782, which claims priority to PCT/US2005/006334 filed on Feb. 25, 2005 (Lee-Sepsick et al. listed as inventors and Femasys Inc. listed as Applicant).
Response to Office Action filed Nov. 4, 2010 for Japanese Application No. JP2007-500782, which claims priority to PCT/US2005/006334 filed on Feb. 25, 2005 (Lee-Sepsick et al. listed as inventors and Femasys Inc. listed as Applicant).
Decision to Grant issued Apr. 19, 2011 for Japanese Application No. JP2007-500782, which claims priority to PCT/US2005/006334 filed on Feb. 25, 2005 (Lee-Sepsick et al. listed as inventors and Femasys Inc. listed as Applicant).
Restriction Requirement issued Jun. 9, 2010 for U.S. Appl. No. 12/240,738, filed Sep. 29, 2008 (Lee-Sepsick et al. listed as inventors).
Response to Restriction Requirement filed Oct. 11, 2010 for U.S. Appl. No. 12/240,738, filed Sep. 29, 2008 (Lee-Sepsick et al. listed as inventors).
Non-Final Office Action issued Dec. 21, 2010 for U.S. Appl. No. 12/240,738, filed Sep. 29, 2008 (Lee-Sepsick et al. listed as inventors).
Response to Non-Final Office Action filed Apr. 21, 2011 for U.S. Appl. No. 12/240,738, filed Sep. 29, 2008 (Lee-Sepsick et al. listed as inventors).
Restriction Requirement issued Jun. 9, 2010 for U.S. Appl. No. 12/240,791, filed Sep. 29, 2008 (Lee-Sepsick et al. listed as inventors).
Response to Restriction Requirement filed Oct. 11, 2010 for U.S. Appl. No. 12/240,791, filed Sep. 29, 2008 (Lee-Sepsick et al. listed as inventors).
Non-Final Office Action issued Dec. 21, 2010 for U.S. Appl. No. 12/240,791, filed Sep. 29, 2008 (Lee-Sepsick et al. listed as inventors).
Response to Non-Final Office Action filed Apr. 21, 2011 for U.S. Appl. No. 12/240,791, filed Sep. 29, 2008 (Lee-Sepsick et al. listed as inventors).

Abma, J.C., Chandra A., Mosher, W.D. et al., "Fertility, family planning, and women's health: new data from the 1995 National Survey of Family Growth," *Vital Health Stat.*, 1997, vol. 23, No. 19.
ACOG Practice Bulletin 46: "Clinical management guidelines for obstetrician-gynecologists," *Obstetrics and Gynecology*, 2003, vol. 102, pp. 647-658.
American Foundation for Urologic Disease, "Facts about vasectomy safety", May, 5, 2004.
Canavan , T. "Appropriate use of the intrauterine device," *American Academy of Family Physicians*, Dec. 1998.
Clenney, T. et al., "Vasectomy Techniques," *American Academy of Family Physicians*, Jul. 1999.
"Fertility, Contraception and population policies," *United Nations Population Division, Department of Economic and Social Affairs*, Apr. 25, 2003, ESA/P/WP.182.
Hendrix N. et al., "Sterilization and it consequences," *Obstetrical and Gynecological Survey*, vol. 54, No. 12, Dec. 1999, p. 766.
Holt, V.L. et al. "Oral contraceptives tubal sterilization, and functional ovarian cyst risk," *Obstetrics Gynecology*, 2003, vol. 102, pp. 252-258.
Jamieson, D.J. et al., "A comparison of women's regret after vasectomy versus tubal sterilization," *Obstetrics Gynecology*, 2002, vol. 99, pp. 1073-1070.
Snider, S., "The pill: 30 years of safety concerns," *U.S. Food and Drug Administration*, Apr. 2001.
Viddya Medical News Service, "Side effects of tubal ligation sterilizations," vol. 1, Issue 249, 2000.
Abdala, N. et al., "Use of ethylene vinyl alcohol copolymer for tubal sterilization by selective catheterization in rabbits," J. Vasc. Interv. Radiol. Aug. 2001, 12(8), pp. 979-984.
Pelage, J.P. et al., "Selective salpingography and fallopian tubal occlusion with n-butyl-2-cyanoacrylate: report of two cases," Radiology, Jun. 1998, vol. 207, No. 3, pp. 809-812.
Van der Leij, G. et al., "Radiographic aspects of office hysteroscopic tubal occlusion with siloxane intratubal devices (the Ovabloc method)," Int. J. Gynaecol. Obstet., Nov. 1997, vol. 59 No. 2, pp. 123-131.
Maubon A.J. et al., "Tubal sterilization by means of selective catheterization: comparison of a hydrogel and a collagen glue," J. Vasc. Interv. Radiol., Sep.-Oct. 1996, vol. 7, No. 5, pp. 733-736.
Berkey, G.S. et al., "Sterilization with methyl cyanoacrylate-induced fallopian tube occlusion from a nonsurgical transvaginal approach in rabbits," J. Vasc. Interv. Radiol., Sep.-Oct. 1995, vol. 6, No. 5, pp. 669-674.
Van der Leij, G. et al., "Impact of Ovabloc intratubal polymer on the morphology of the fallopian tube," Int. J. Gynecol:Pathol., Apr. 1995, vol. 14, No. 2, pp. 167-173.
Huvar, I. et al., "Hysteroscopic sterilization using Ovabloc," Ceska Gynekol, Aug. 1994, vol. 59, No. 4, pp. 193-195.
No authors listed, "Hysteroscopy ACOG Technical Bulletin No. 191—Apr. 1994," Int. J. Gynaecol. Obstet., May 1994, vol. 45, No. 2, pp. 175-180.
Assaf, A. et al. "Histopathological effects of silicone rubber 'Ovabloc' on the human fallopian tube," Int. J. Gynaecol. Obstet., Nov. 1993, vol. 43, No. 2, pp. 181-189.
Cooper, J.M., "Hysteroscopic sterilization," Clin. Obstet. Gynecol., Jun. 1992, vol. 35, No. 2, pp. 282-298.
Su, Y.K. "Embolus formation using bismuth polyurethane for tubosterilization observation of 259 cases," Zhonghua Fu chan Ke Za Zhi, Nov. 1991, vol. 26, No. 6, pp. 352-354, p. 388.
Brundin, J., "Transcervical sterilization in the human female by hysteroscopic application of huydrogelic occlusive devices into the intramural parts of the fallopian tubes: 10 years experience of the P-bock," Eur. J. Obstet. Gynecol. Reprod. Biol., Mar. 21, 1991, vol. 39, No. 1, pp. 41-49.
Chen, F.Q. "Study on the transperitonea sterilization of the fallopian tube with silicon rubber plug and its reversibility," Shengzhi Yu Biyun, Aug. 1989, vol. 9, No. 3, pp. 51-54.
Reed T.P. et al., "Tubal Occlusion with Silicone Rubber," J. Reprod. Med., Jul. 1980, vol. 25, No. 1, pp. 25-28.
Loffer, F.D. et al. "Learning hysteroscopy sterilization and the Ovabloc System with Hyskon," Acta Fur Fertil., Nov.-Dec. 1986; vol. 17, No. 6, pp. 477-480.

Brundin, J. et al, "Long-term toxicity of a hydrogelic occlusive device in the isthmus of the human oviduct. A light microscopic study.," Acta. Pathol. Microbiol. Immunol. Scand. [A], May 1985, vol. 121, No. 6.

Loffer, F.D., "Hysteroscopic sterilization with the use of formed-in-place silicone plugs," Am. J. Obstet. Gynecol., Jun. 1, 1984, vol. 149, No. 3, pp. 261-270.

Dan, S.J. et al. "Fallopian tube occlusion with silicone: radiographic appearance," Radiology, Jun. 1984, vol. 151, No. 3, pp. 603-605.

Fischer, M.E. et al. "Silicone devices for tubal occlusion: radiographic description and evaluation," Radiology, 1984, vol. 151, No. 3, pp. 601-602.

ApSimon, H.T. et al. "Embolizatio of small vessels with a double-lumen microballoon catheter. Part I: Design and construction," Radiology, Apr. 1984, vol. 151, No. 1, pp. 55-57.

Neuwirth, R.S. et al., "Trials with the FEMCEPT method of female sterilization and experience with radiopaque methylcyanoacrylate," Am. J. Obstet. Gynecol., Apr. 1983, vol. 145, No. 8, pp. 948-954.

Reed, T.P. et al., "Hysteroscopic tubal occlusion with silicone rubber," obstet. Gynecol., Mar. 1983, vol. 61, No. 3, pp. 388-392.

Loffer F.D. "What's new I female sterilization? The silicone tubal plug is.," Ariz. Med., Jul. 1982, vol. 39, No. 7, pp. 442-445.

Richart R.M. "Female sterilization using chemical agents," Res. Front. Fertil. Regul., Dec. 1981, vol. 1, No. 5, pp. 1-12.

Neuwirth, R.S. et al., "An outpatient approach to female sterilization with methylcyanoacrylate," Am. J. Obstet. Gynecol., Apr. 1, 1980, vol. 136, No. 7, pp. 951-956.

Davis, R.H. et al., "chronic occlusion of the monkey fallopian tube with silicone polymer," Obstet. Gynecol., Ar., 1979, vol. 53, No. 4, pp. 527-529.

Reed, T.P. et al., "Hysteroscopic Oviductal Blocking with Formed-In-Place Silicone Rubber Plugs II Clinical Studies." Paper presented at the Clinical Symposium on Gynecologic Endoscopy Seventh Annual Meeting, Hollywood, FL, Nov. 17, 1978, p. 1-4.

Davis, R.H. et al., "chronic occlusion of the rabbit Fallopian tube with silicone polymer," Gynecol. Obstet. Invest., 1979, vol. 10, No. 6, pp. 281-288.

Steptoe, P.C., "Advances in laparoscopic sterilization techniques," S. Afr. Med., Nov. 1975, vol. 49, No. 48, pp. 2019-2021.

Farcon, E. et al., "An absorbable intravasal stent and a silicone intravasal reversible plug. Report of experiments on animals.," Invest. Urol., Sep. 1975, vol. 13, No. 2, pp. 108-112.

Davis, R.H. et al., "Fallopian tube occlusion in rabbits with silicone rubber," J. Reprod. Med., Feb. 1975, vol. 14, No. 2, pp. 56-61.

No authors listed, "Implants seen as reversible contraceptives," Biomed. News., Nov. 1973, vol. 4, p. 12.

Libenzon, L.L. et al.,."Contraception through the sealing off of Fallopian tubes (experimental studies),"Eksp. Khir. Anesteziol., Sep.-Oct. 1973, vol. 18, No. 5, pp. 18-20.

No authors listed, "Animal studies show silicone plugs prevent conception," JAMA, Jul. 9, 1973, vol. 225, No. 2, pp. 105-106.

Stevenson, T.C. et al., "The effect of methyl cyanoacrylate tissue adhesive on the human Fallopian tube and endometrium," J. Obstet. Gynaecol. Br. Commonw., Nov. 1972, vol. 79, No. 11, pp. 1028-1039.

Grode, G.A. et al. "Feasibility study on the use of a tissue adhesive for the nonsurgical blocking of fallopian tubes. Phase I: evaluation of a tissue adhesive," Fertil. Steril., Sep. 1971, vol. 22, No. 9, pp. 552-555.

Neuwirth, R.S. et al., "chemical induction of tubal blockade in the monkey," Obstet. Gynecol., Jul. 1971, vol. 38, No. 1, pp. 51-54.

Omran K.F. et al., "Tubal occlusion: a comparative study," Int. J. Fertil., Oct.-Dec. 1970, vol. 15, No. 4, pp. 226-241.

Rakshit, B."Attempts at chemical blocking of the Fallopian tube for female sterilization," J. Obstet. Gynaecol., India, 1970, vol. 20, pp. 618-624.

Harrell, W.B. et al., "Simulated tuboplasty using tissue adhesive on uterine horn in canines," J. Ark. Med. Soc., Apr. 1969, vol. 65, No. 11, pp. 433-435.

Erb, R.A. et al. "Hysteroscopic Oviductal Blocking with Formed-in-Pace Silicone Rubber Plugs," J. Reprod. Med., Aug. 1979, vol. 23, No. 2, pp. 65-68.

Hefnawi F. et al., "Control of fertility by temporary occlusion of the oviduct," Am. J. Obstet Gynecol., Oct. 1, 1967, vol. 99, No. 3, pp. 421-417.

* cited by examiner

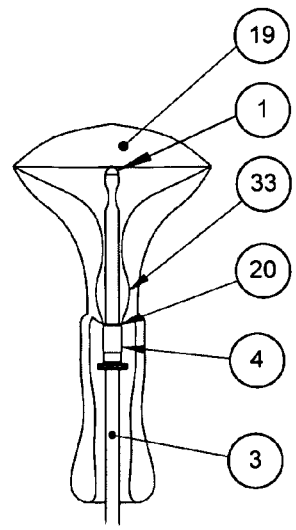
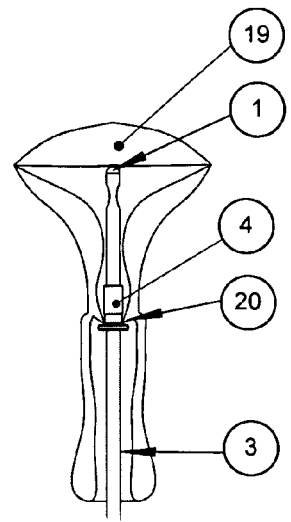
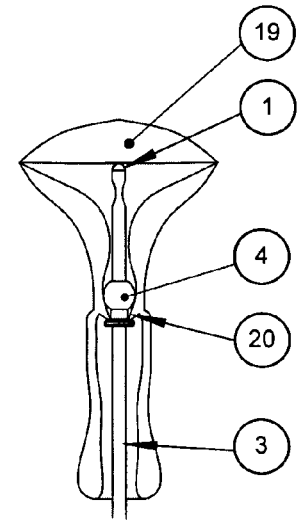
Figure 4A          Figure 4B          Figure 4C
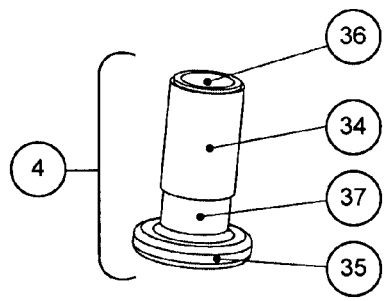
Figure 4D
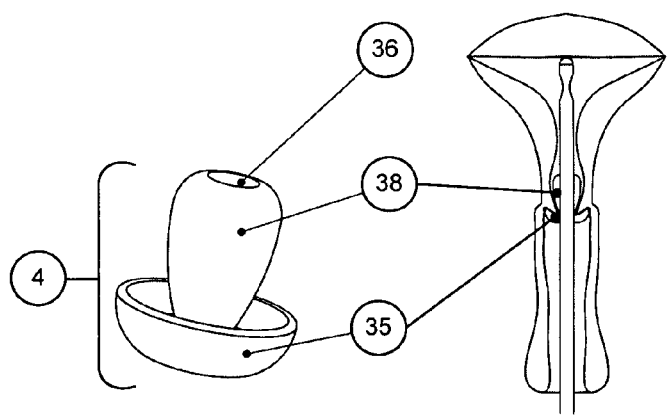
Figure 4F          Figure 4G
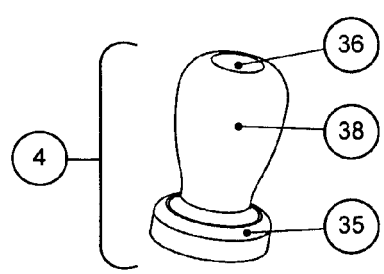
Figure 4E

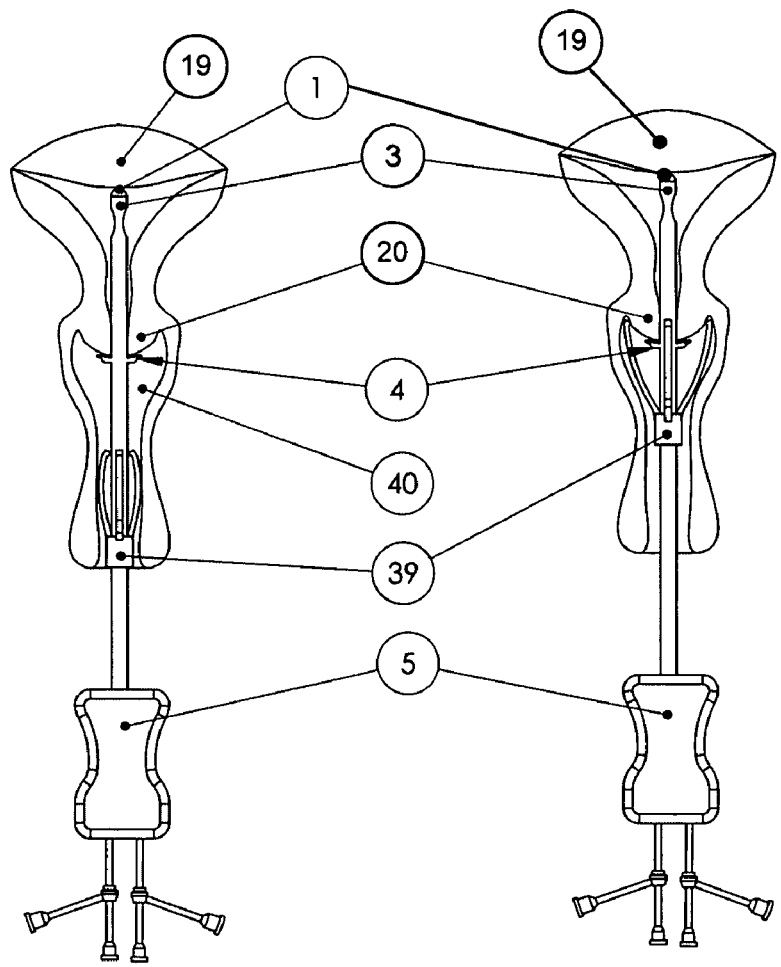
Figure 5A
Figure 5B
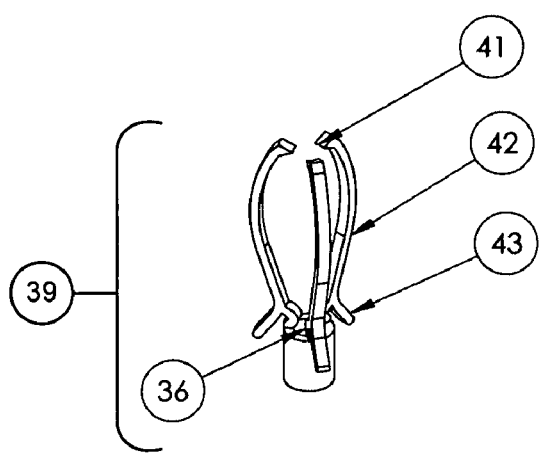
Figure 5C
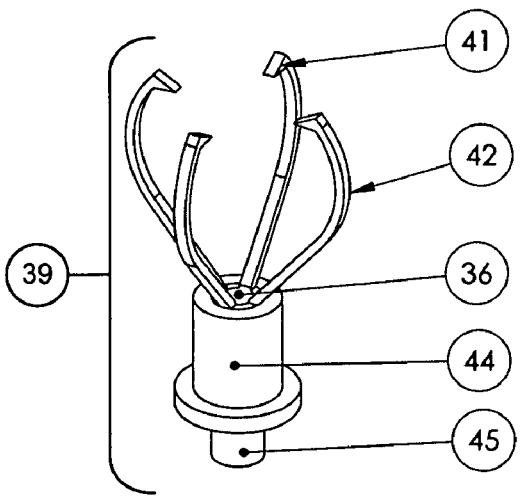
Figure 5D

METHODS AND DEVICES FOR CONDUIT OCCLUSION

CROSS-REFERENCE TO A RELATED APPLICATION

This application claims the priority of U.S. Provisional Patent Application 60/547,491, filed Feb. 25, 2004, and U.S. Provisional Patent Application 60/587,604, filed Jul. 13, 2004, both of which are herein incorporated by reference in their entirety.

TECHNICAL FIELD

The present invention relates to methods and devices for occluding conduits. In particular, the present invention is directed to methods and devices for delivery of compositions that lead to occlusion of conduits and for later re-opening of such occluded conduits.

BACKGROUND OF THE INVENTION

In the medical and research fields, there are many clinical situations where it is desired or necessary to stop the passage, flow or transfer of substances within a body tube or conduit by causing an occlusion or blockage. It is often desirable for the occlusion to be re-opened at a later time. Unfortunately, many occlusion techniques are often harmful or potentially harmful and are not reversible to accommodate changes in the needs or desires of patients.

One area that has a need for reversible occlusion of a body tube is the control of fertility. Over the last 50 years, the world has experienced the highest rates of population growth and the largest annual population increases recorded in history. Women account for over 50% of the world's population and play a critical role in family health, nutrition, and welfare. One of the most significant areas in need of attention and innovation in women's healthcare is that of contraception, where the reproductive aged woman is currently faced with sub-optimal alternatives.

Over the past 20 years, couples in every world region have adopted contraception with increasing frequency as a means of regulating the timing and number of children. However, in the less developed countries there are still a substantial number of women, who wish to control fertility but are not presently using contraception. Many governments worldwide are intervening with policies to provide access to contraceptive methods to control over-population. In 2000, it was estimated that 123 million women did not have access to safe and effective means of contraception. Therefore, the potential for a suitable contraceptive system has widespread implications for the world population.

Today there are several contraceptive options available, although currently available options are associated with specific limitations. Some contraceptive options include surgical intervention, such as tubal ligation for female sterilization and vasectomy for male sterilization, both of which are invasive and considered non-reversible. Other options available to women are hormonal contraceptives, which are not suitable or safe for a number of women. Further options include intrauterine devices that may have significant side effects. The ideal contraceptive system is one that would provide an immediately effective, reversible, non-hormonal, non-surgical, easy to deliver, office-based solution that does not require anesthesia, patient compliance, or special equipment, and does not leave a foreign body in place long-term. None of the current options meets these requirements.

The most widely utilized method of permanent contraception is tubal ligation or female surgical sterilization. There are a number of major drawbacks associated with tubal ligation. The procedure is permanent and invasive, requires general anesthesia, has a long recovery time, and can result in post-tubal ligation syndrome. Post-tubal ligation syndrome occurs when the surgeon closing the fallopian tube inadvertently damages or destroys blood vessels to the ovaries causing post-menopausal symptoms of abnormal bleeding, memory loss, confusion, mood swings, and lack of sex drive. In addition, a recent study has found that of all the hormonal and non-hormonal methods of birth control, tubal sterilization has the greatest association with development of functional ovarian cysts. Further, women who undergo tubal ligation frequently express regret or seek reversal. Reversal of tubal ligation, when attempted, is difficult, costly, and frequently unsuccessful.

On the other end of the spectrum, the most widely utilized method of non-surgical contraception is the administration of hormonal drugs, such as implanted hormones or birth control pills. This method of contraception is effective only so long as hormones are administered or birth control pills taken according to a specific regimen. Although widely used, this method of contraception is not suitable or safe for all women. In addition, there is a high failure rate resulting in unintended pregnancies due to patient non-compliance with the daily regimen of taking pills.

One reversible contraceptive device currently available is the intrauterine device (IUD). There are an estimated 85 to 100 million women worldwide using this method, substantiating the importance of reversibility. However, given the possible health risks associated with IUDs and patient reluctance to have a foreign body in place for an extended period of time, fewer than 1 million women in the U.S. use this method, and many manufacturers have ceased distribution of these devices. The health risks include unplanned expulsion requiring removal due to excessive pain or bleeding, pelvic-inflammatory disease, permanent infertility, ectopic pregnancy, miscarriage and even death.

While the currently available compositions and methods for contraception represent a significant advancement in the art, further improvements would be desirable to provide safe, effective and reversible non-surgical devices, compositions, and methods for preventing pregnancy. It would be beneficial if these devices, compositions and methods provided an immediately effective, non-hormonal, non-surgical, easy to deliver, office-based solution that did not require anesthesia or patient compliance with a daily regimen. It would be further beneficial if these devices, compositions and methods did not require special equipment to undertake a contraceptive procedure or require a foreign body remaining in place over a long period of time. It would be further beneficial if these devices, compositions and methods were suitable to reversal. Some or all of these advantages of an ideal contraceptive system are provided by the devices, systems, compositions and methods of the present invention.

SUMMARY

The present invention comprises methods, systems, and devices for the delivery of compositions for the occlusion of conduits. In particular, the present invention comprises methods, systems, and devices for the occlusion of conduits in humans or other animals. The devices of the present invention are used to deliver compositions comprising materials that occlude the conduit. The conduit may be a naturally occurring conduit such as a tube or vessel in the body or may be a conduit that has been introduced in the body such as a medical device or through surgical means. The occlusive material may be a permanent implant or may be a material that is degraded or resorbed by the body and allows for tissue ingrowth to maintain the occlusion.

The present invention also comprises delivery systems, methods, and devices for reversing the occlusion. The occlusion may be reversed by removal of implant materials or tissue ingrowth that are blocking the conduit, by creating a channel through the occlusion, or by creating a new channel around the occlusion.

One aspect of the present invention comprises delivery systems, methods and devices for occlusion of fallopian tubes and reversal of the occlusion. One embodiment of this aspect is a method that comprises introduction of a delivery device system for delivery of occlusive material to both fallopian tubes without the necessity to remove, reinsert, or substantially reposition the delivery device. Such a device may be sized for each recipient by pre-visualization of the anatomy of the recipient. The implanted occlusive material may be permanent or may be degraded or resorbed by the body and replaced by ingrowth of tissue. Reversal of such occlusion comprises a device that is capable of removing the occlusive material. In another embodiment, reversal of conduit occlusion comprises a device that is capable of forming a channel through or around the material or ingrown tissue. Reversal of conduit occlusion may further comprise placement of devices, such as stents, to maintain the re-opened channel; these methods of maintaining the re-opened conduit are also performed through the use of the delivery device.

BRIEF DESCIPTION OF DRAWINGS

FIGS. 4A-C show an embodiment of a delivery device stabilizer and its placement within a body. 4A shows an embodiment of a delivery device stabilizer prior to placement in the body. 4B shows the delivery device stabilizer in place, prior to expansion of the expandable portion. 4C shows the expandable portion expanded.

FIG. 4D shows an embodiment of a delivery device stabilizer that is slidable on the introducer shaft and incorporates an expandable portion, that is shown unexpanded.

FIG. 4E shows an embodiment of a pre-formed delivery device stabilizer that is slidable on the introducer shaft.

FIG. 4F shows an embodiment of a delivery device stabilizer mechanism that is slidable on the introducer shaft and incorporates a cup-shaped base that fits over the cervix.

FIG. 4G shows the interaction of the delivery device stabilizer shown in FIG. 4F with outer face of the cervix.

FIG. 5 shows a cervical clamp and its placement. FIG. 5A shows an embodiment of the delivery device in position in a body, incorporating a cervical clamp. FIG. 5B shows an embodiment of the delivery device in position in a body with the cervical clamp in position. FIG. 5C shows aspects of an embodiment of a cervical clamp. FIG. 5D shows aspects of an embodiment of a cervical clamp.

FIG. 6 shows embodiments of methods and devices for opening of occlusions.

Figure 6A:
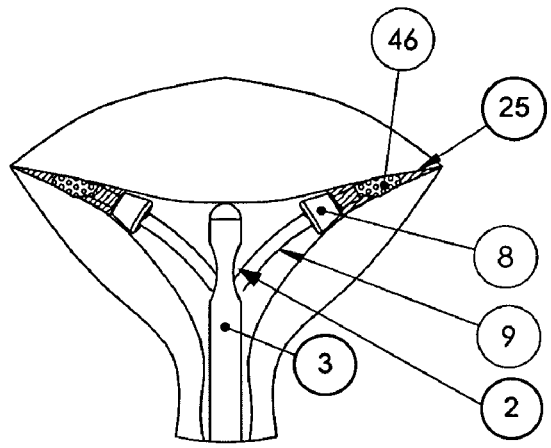
Figure 6B:
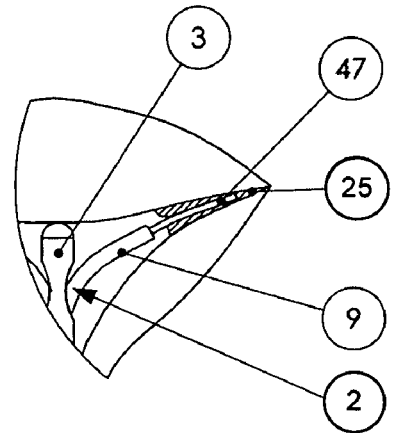
Figure 6C:
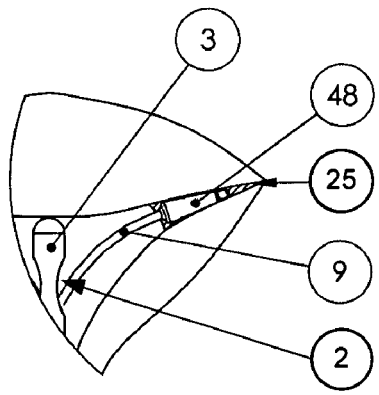
Figure 6D:
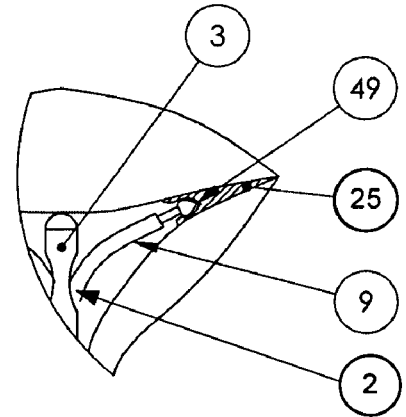
Figure 6E:
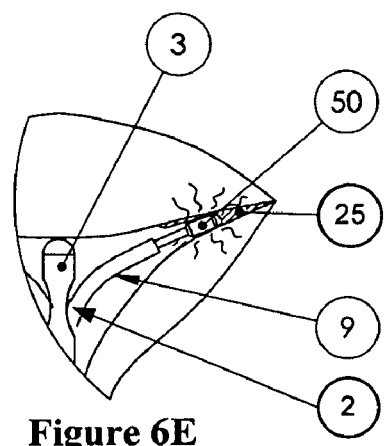
Figure 6F:
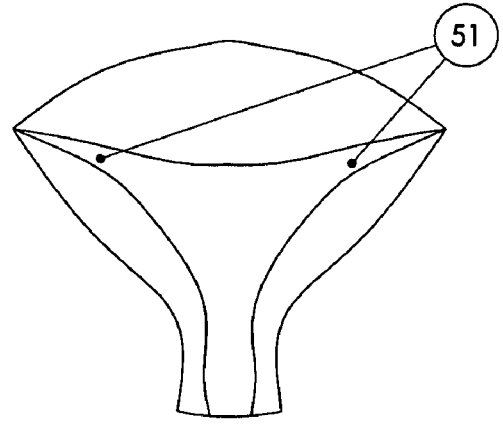

FIG. 6A shows an embodiment of delivery of one or more solutions that degrade and remove the occlusion. FIG. 6B shows an embodiment of use of a guide wire or catheter to open the occlusion. FIG. 6C shows an embodiment of use of an expandable member, such as a balloon, to open the occlusion. FIG. 6D shows an embodiment of use of a cutting or debriding member to open the occlusion. FIG. 6E shows an embodiment of an energy device to open the occlusion. FIG. 6F shows an embodiment of the conduits after opening.

DETAILED DESCRIPTION

The present invention comprises delivery systems, methods and devices for occluding conduits, and methods, systems, and devices for reversing occlusions in conduits. The present invention comprises delivery systems and methods for occluding conduits in the body through the placement of occlusive material using a delivery device. One aspect of the present invention comprises occluding conduits permanently. In another aspect, the present invention comprises reversibly occluding conduits. Yet another aspect of the present invention comprises methods, delivery systems and compositions to occlude the fallopian tubes of a female mammal, and methods and systems to re-open such occlusions. A further aspect of the invention comprises methods, delivery systems, and compositions to occlude the vas deferens of a male mammal, and methods and systems to re-open such occlusions. Methods, systems and compositions of the present invention may be used in embodiments that permit non-surgical, office-based reversible sterilization.

The present invention comprises methods for occluding conduits, particularly conduits found in human or other animal bodies. Such conduits may exist naturally in the body or be present because of disease, damage, placement of medical devices or surgical means.

As used herein, the term "conduit" shall refer to any tube, duct, or passage, whether natural or synthetic, which carries gas, fluids or solids in a biological system.

As used herein, "occlude" refers to blocking, partially or fully, the transport of gas, fluids, or solids through a conduit. The term "occlusion," as used herein, refers to blockage within a conduit wherein such blockage results in partial restriction or complete interruption of the transport of gas, fluids, or solids through the conduit. As used herein, "occlusive material" refers to a composition that is capable of occluding a conduit by effecting an occlusion therein. As used herein, occlusive or occluding material means the initial composition that is placed or inserted into the conduit, as well as the composition, whether the physical, biological, or chemical nature of the composition has changed or not, that is in place in the conduit and provides for the interruption of flow through the conduit. The meaning of the term can be determined from its use in the sentence. Occlusive compositions, occlusion compositions, occlusive materials and occlusion materials are terms used interchangeably herein.

As used herein, occlusive material comprises any natural or synthetic compositions or any combination of natural and synthetic compositions that can be placed at the desired site in the conduit using the delivery systems of the present invention. Occlusive materials of the present invention may comprise materials that are fluid, semi-solid, gels, solids, and combinations thereof. The occlusive materials may further comprise a pre-formed material that is of a shape or size that occludes the conduit or may be a material that will take on a form or shape or size to occlude the conduit. Occlusive materials may further comprise compositions that cure in situ at the desired site in the conduit. The occlusive compositions may further comprise materials that polymerize in situ, wherein the polymerization may be initiated either at the site of interest in the conduit or prior to placement at the site. Occlusive compositions may further comprise combinations of two or more of any of the foregoing materials. Disclosed herein are exemplary compositions and materials suitable for use as occlusive compositions.

As used herein, "cure" means a change in the physical, chemical, or physical and chemical properties of the occlusive material following placement or insertion at the desired site in a conduit.

As used herein, non-invasive visualization or imaging refers to all forms of imaging that do not require the use of ionizing radiation or direct visualization such as by hysteroscopy. Examples of non-invasive imaging include all forms of ultrasound or magnetic resonance imaging, which are incorporated within the scope of this definition.

As used herein, the term "delivery system" comprises all components necessary to deliver an occlusive material or all components necessary to open an occlusion, and may comprise an introducer, delivery device or catheter(s), combinations thereof, occlusion means or means for opening an occlusion, and any other components necessary for the full functioning of the delivery system.

In general, the methods of the present invention comprise administration of delivery systems that deliver compositions that are capable of occluding conduits. The delivery systems comprise devices that are capable of delivering occlusive compositions to the desired site. Disclosed herein are exemplary methods, delivery systems, and compositions for occlusion of conduits of the reproductive tracts of mammals. Such methods and compositions can be used in other physiological systems and biological sites of humans or other animals, and delivery systems for such biological sites are contemplated by the present invention.

The present invention also comprises methods for opening, generally the re-opening, of occluded conduits. The methods comprise means for removal of the occlusion, including removal of occluding compositions or for formation of openings or channels through or around one or more occluded regions. Means of removal include, but are not limited to, physical withdrawal of the occluding composition, destruction of the occluding composition using physical, chemical or biological means, canalization of the one or more occluded regions, and placement of new conduits, such as stents or bypass materials to restore functionality to the formerly occluded region. Disclosed herein are exemplary methods, delivery systems and compositions for removal of the occlusion of conduits of the reproductive tracts of mammals to restore fertility functionality. Such restorative methods and compositions can be used in other physiological systems and biological sites of humans or other animals, and delivery systems for such biological sites are contemplated by the present invention.

One aspect of the present invention comprises methods of contraception for mammalian females that uses ultrasound visualization of a delivery system that delivers a resorbable composition to a target site, for example, from the cornual aspect of the uterus into each fallopian tube, wherein the composition is capable of creating an occlusion in each fallopian tube.

A further aspect comprises using the delivery system to implant occlusive material. One aspect comprises methods that use ultrasound for visualization and positioning of the device and monitoring and confirming the placement of the composition when an ultrasound visible composition is used. The method comprises introduction of the device, including inserting the shaft of the introducer through the cervix until the atraumatic tip contacts the uterine fundus as determined by non-invasive visualization such as ultrasound or through the sensation of the operator. When the tip is appropriately placed, optionally, the operator may engage a member that aids in stabilizing the delivery device, referred to herein as a delivery device stabilizer. For example, this member may be a depth stop, a member which indicates that the tip is in position and the introducer shaft should be not be introduced any further, and includes, but is not limited to, other delivery device stabilizers such as those shown in FIGS. 4 and 5, or more than one member that aids in stabilization. With the introducer in position, each of two double-lumen balloon catheters is introduced through an introducer channel until it exits the channel in the shaft of the introducer, and the tip of the catheter is located within the uterine cornua as determined by ultrasound.

A further aspect of the present invention comprises methods wherein each catheter undergoes the following steps. At a proximal end of the catheter, one end of the catheter which is near the handle and distant from the delivery end of the catheter, a cartridge containing balloon distension medium is connected to the balloon fitting, the stopcock is opened, and the distension medium is delivered to effect inflation of the balloon positioned at the delivery end of the catheter. The stopcock is then closed and the cartridge is disconnected from the fitting. At a proximal end of the catheter, a cartridge containing the occlusive composition is then connected to the delivery catheter fitting, the material is delivered through the catheter and out of the delivery end of the catheter that is at or adjacent to the delivery site. The material may be delivered directly to the target site or may move from the delivery site to the target site location, and the material cures to form the occlusion. Once the material has at least partially cured into an occlusion, the balloon is deflated. Each catheter is retracted until it is housed within the introducer shaft or fully removed from the introducer. If necessary, the delivery device stabilizer is disengaged. The delivery system is then withdrawn from the patient leaving only the occlusion in place. The occlusive material may be delivered sequentially or simultaneously to the two fallopian tubes. The device is designed for delivery of occlusive compositions to two separate sites with minimal to no repositioning and without removal of the device, including the introducer, until the procedure is complete. One or both of the delivery catheters may be retracted into the introducer without repositioning or removal of the entire device.

Yet another aspect of the present invention comprises a delivery system for implantation of the occlusive composition into the fallopian tubes comprising a delivery device comprising an introducer with two channels, optionally one or more delivery device stabilizers, a housing means which may function as a handle if needed, means for attachment of one or more containers of balloon distension medium and the occlusive composition, and two catheters for delivery of the occlusive composition. The catheters may comprise an end structure, which is a balloon or other similarly functioning member that may hold the catheter in position, prevents leakage of the material from the target site or performs both functions. The occlusive composition may be mixed prior to delivery and then delivered from the container through the catheters to one or more target sites.

One aspect of the present invention comprises a delivery system comprising an introducer, one or more catheters wherein each may have a distinct function or design, and one or more cartridge components wherein each cartridge may have a distinct design and contain a distinct material.

Figure 1A:
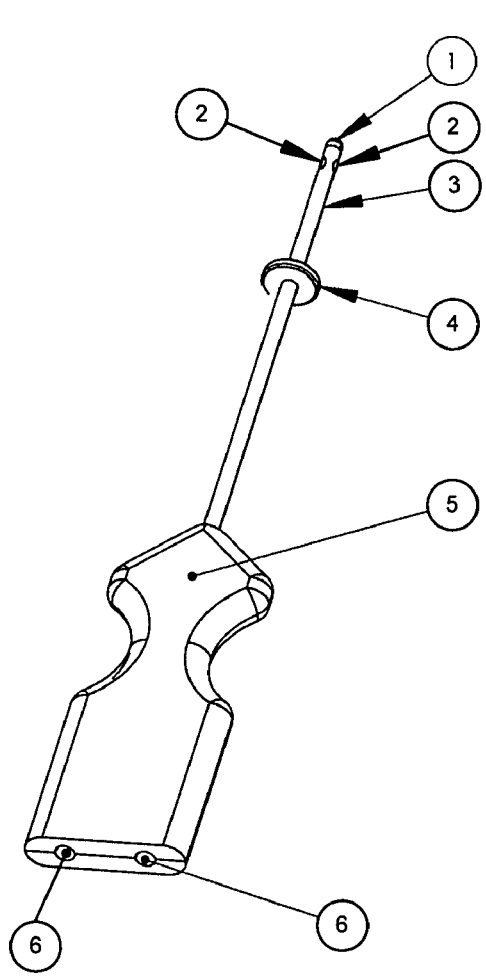
FIG. 1A shows an embodiment of a delivery device for the transcervical delivery of occlusive material.

Now referring to FIG. 1A, an exemplary embodiment of an introducer is shown comprising the following subcomponents: the introducer tip (1) which is shaped for atraumatic insertion through the cervix; the introducer shaft (3), generally a structure which may be cylindrical in nature, which contains two introducer shaft catheter channels (2), which run the interior length of the shaft and have openings for insertion of a catheter into the shaft and for the catheter to exit the shaft; a delivery device stabilizer (4) which in this example indicates the position of the tip relative to the point of entry, which may be measured based on markings along the shaft and which may further serve to hold the introducer in position; a handle (5) which has an ergonomic design for gripping by the operator; and a pair of catheter insertion holes (6) through which the delivery catheters can be inserted into the introducer and guided to the introducer shaft catheter channels (2). The delivery device stabilizer (4) shown in this example is a depth stop.

Figure 1B:
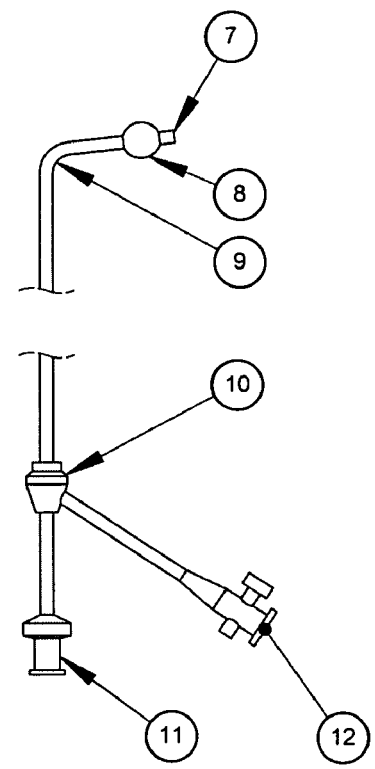
FIG. 1B shows an embodiment of a double lumen catheter.

FIG. 1B shows a delivery catheter for delivery of occlusive material, said catheter comprising the following subcomponents: the delivery end (7) of the catheter through which the occlusive material is delivered to the target site; a balloon (8) which may hold the catheter in position and may prevent leakage of the occlusive material away from the target; the shaft of the catheter (9) which, in this figure, features a preformed curve designed to aid in movement of the delivery end of the catheter from the introducer shaft into the cornual aspect of the uterus, and includes two lumens, one for inflation of the balloon and one for delivery of the occlusive material; a bifurcation (10) of the catheter lumens; a fitting (11) that mates with a cartridge that contains flowable material to be delivered, such as the occlusive material; and a fitting with a stopcock (12) that mates with a cartridge that contains flowable material to be delivered, such as distension media for inflation and deflation of the balloon. One aspect of the present invention comprises a delivery catheter that is a double lumen delivery catheter. It should be understood that the delivery catheter may comprise a number of features and designs known in the art for catheters and that would be useful for the function of the delivery system. In one embodiment of the present invention, the one or more catheters are disposed within the hollow introducer shaft. The catheters of the present invention may be single lumen or dual lumen catheters, or other catheters that would function in the present invention. One aspect of the invention comprises a stopcock is used to prevent leakage of the balloon distension medium after placement. It should be understood that other devices, such as a valve or diaphragm, including a self-sealing diaphragm, may also serve the same function and be useful in obtaining and maintaining inflation of the balloon of the present invention.

Figure 1C:
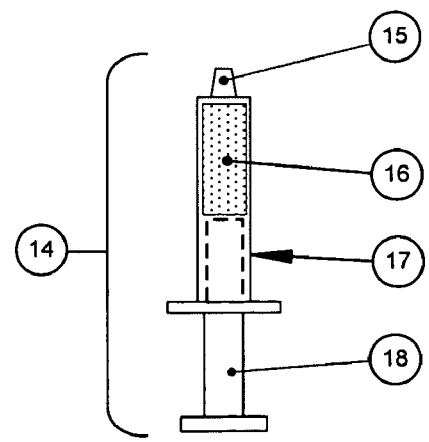
FIG. 1C shows an embodiment of a cartridge component containing a flowable material, which includes, but is not limited to occlusive material or balloon distension material.

FIG. 1C shows a cartridge (14) which may contain a flowable material (16) wherein the cartridge component comprises the following aspects: the tip of the cartridge (15) that mates with the delivery catheter fitting (11) or a fitting with stopcock (12) as required; the barrel of the cartridge (17); a plunger (18) that fits with the barrel of the cartridge (17) so as to form a seal to prevent back-flow of flowable material, said plunger allowing the operator to deliver the flowable material; and a flowable material (16), wherein the flowable material may comprise occlusive material or distension media.

Figures 2A, 2B, 2C:
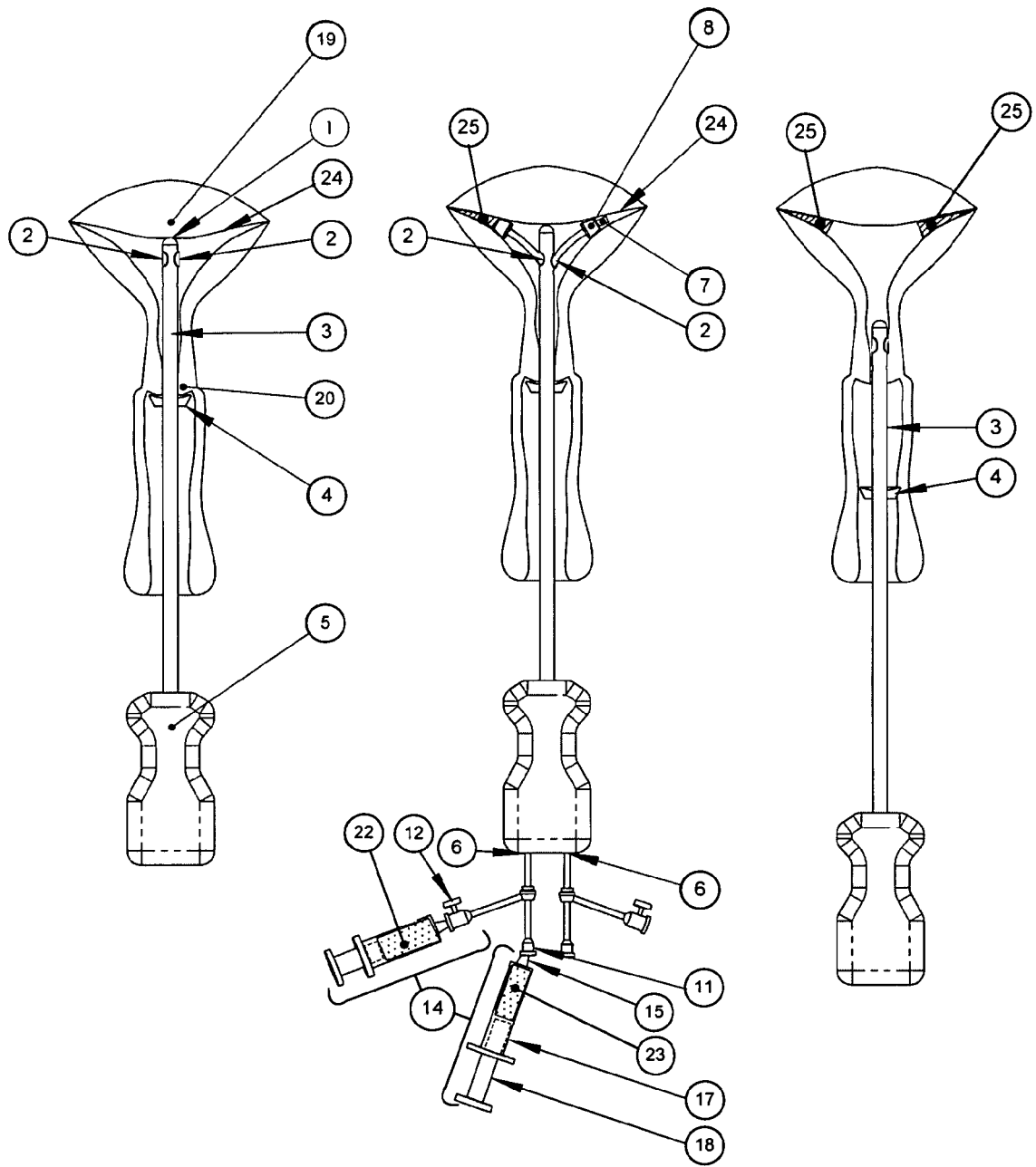
FIG. 2A shows a step in an embodiment of a method of the delivery system for deploying and using a delivery device wherein the introducer is inserted through the cervix.
FIG. 2B shows a step in an embodiment of a method of the delivery system for deploying and using a delivery device wherein two double lumen catheters are deployed contralaterally within the uterine cornua.
FIG. 2C shows a step in an embodiment of a method of the delivery system, wherein each catheter is retracted and the operator begins to withdraw the introducer shaft from the uterus.

Now referring to FIGS. 2A-2C, wherein a schematic is shown of an exemplary embodiment of a method for deploying and using the exemplary delivery system shown in FIG. 1 to effect an occlusion in both fallopian tubes of a mammal. It should be understood that not all steps need be performed in every deployment. Further, it should be understood that additional steps may be added as determined by one skilled in the art as necessary to increase performance, efficacy, or comfort of the subject undergoing the method depicted in FIG. 2.

In FIG. 2A, the operator holds the introducer handle (5) and inserts the shaft of the introducer (3) through the cervix (20) until the atraumatic tip (1) contacts the uterine fundus (19) as determined by tactile feel, non-invasive visualization such as ultrasound, or a combination of both tactile feel and non-invasive visualization. When the atraumatic tip (1) is appropriately placed, the introducer shaft catheter channels (2) are located such that the openings are directed toward the uterine cornua (24). Following contact of the atraumatic tip (1) with the uterine fundus (19), the delivery device stabilizer (4) is moved into position. In one embodiment, the delivery device stabilizer (4) may comprise components or structures that function to ensure that the operator maintains a fixed position of the introducer shaft, for example for preventing uterine perforation, as well as maintaining the position of the shaft catheter channels (2) throughout the procedure. In another embodiment, the delivery device stabilizer (4) may comprise components or structures to provide a depth stop mechanism to the delivery device. In still another embodiment, the delivery device stabilizer comprises components or structures to provide a depth stop mechanism and stabilization to the delivery device.

FIG. 2B depicts the use of the delivery system for the introduction of an in situ curing flowable occlusive material. With the introducer in position, the operator moves each of two double-lumen catheters through a catheter insertion hole (6) through the introducer shaft catheter channels until each catheter exits the introducer shaft catheter channel (2), and the delivery end (7) of the catheter is located within the uterine cornua (24) as determined by the operator's tactile feel, non-invasive imaging such as ultrasound, or a combination of feel and imaging. An exemplary embodiment of a double lumen catheter is described in FIG. 1B. Once the delivery end (7) of the catheter is positioned within the uterine cornua (24), the catheter position may be maintained by a locking mechanism which may be attached to the handle at or near the catheter insertion hole (6), at another location within the handle, or by a mechanism that is separate from the handle and which serves to grab, clamp, hold or otherwise stabilize the catheter such that it does not move and such that the delivery end remains in the target location. In another aspect of the invention, inflation of the balloon as described below is sufficient to maintain position of the catheter, and no additional locking mechanism may be required. A cartridge (14) containing balloon distension medium (22), which has been previously prepared or mixed if such mixing is necessary, is then fitted to a fitting with a stopcock (12), the stopcock is opened, and the distension medium (22) delivered to effect inflation of the balloon (8). Distension medium may comprise any flowable or liquid material suitable for inflation of the balloon (8), such material being chemically compatible with the material of the balloon (8) and may be biologically compatible in the event distension medium is introduced into the uterine cavity or fallopian tubes. Exemplary distension media include, but are not limited to, air and sterile isotonic saline solution. Following inflation of the balloon (8), the stopcock is then closed, the cartridge disconnected from the fitting (12), and the procedure repeated to inflate the balloon on the contralateral side. The balloons may be distended simultaneously using two cartridges. A cartridge (14) containing a flowable occlusive material (23) is then connected to the delivery catheter fitting (11), and the plunger (18) is pressed into the barrel (17) of the cartridge to deliver the flowable occlusive material (23) into and through the catheter, and exiting through the delivery end of the catheter (7) toward the target location for example, where it cures in situ. As depicted in FIG. 2B, occlusive material has been dispensed in the target area and has begun to cure in situ, forming an occlusion (25).

FIG. 2C shows the device at completion of the procedure. Once the flowable occlusive composition has reached the appropriate stage of curing, from beginning to cure to substantially curing into an occlusion (25), the operator uses the distension medium cartridge to deflate each balloon, withdrawing the distension medium into the cartridge. Each catheter is retracted until it is housed within the introducer shaft (3) or, as shown in FIG. 2C, fully removed from the introducer. If necessary, the delivery device stabilizer (4) is disengaged. The delivery device is then withdrawn from the patient, leaving the occlusion in place.

While the exemplary method shown in FIGS. 2A-2C follows a sequence in which both balloons are inflated, occlusive material is delivered through both catheters, both balloons are deflated, and the catheters withdrawn, a procedure in which all actions are completed initially by one delivery catheter followed sequentially by completion of all actions for the second delivery catheter is equally contemplated by the present invention and can be at the discretion of the operator. Further, it should be understood that the exemplary method may comprise, as depicted in FIG. 2B, the sequential dispensing of occlusive material (23) from each of two delivery catheters placed in the uterine cornua (24), or alternatively simultaneous dispensing of occlusive material (23) through both delivery catheters.

Figure 3A:
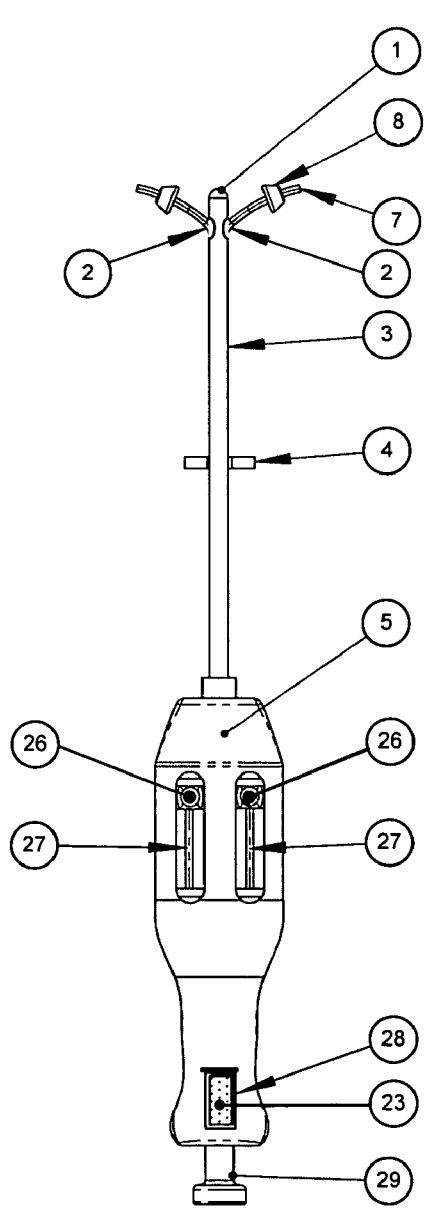
FIG. 3A shows an embodiment of a delivery system, wherein the delivery catheters are shown partially extended.
Figure 3B:
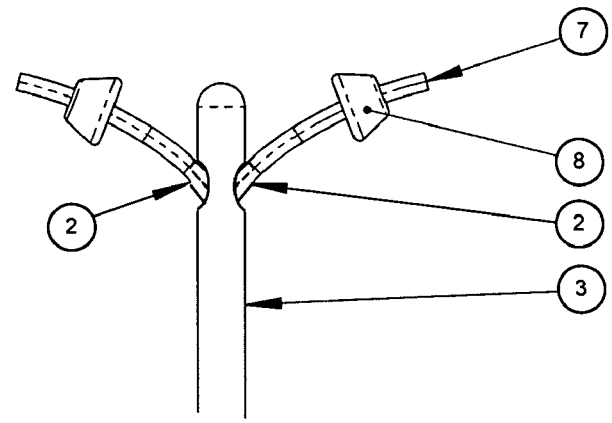
FIG. 3B shows a portion of the delivery system from FIG. 1A wherein the introducer tip and partially extended catheters are shown in greater detail.
Figure 3C:
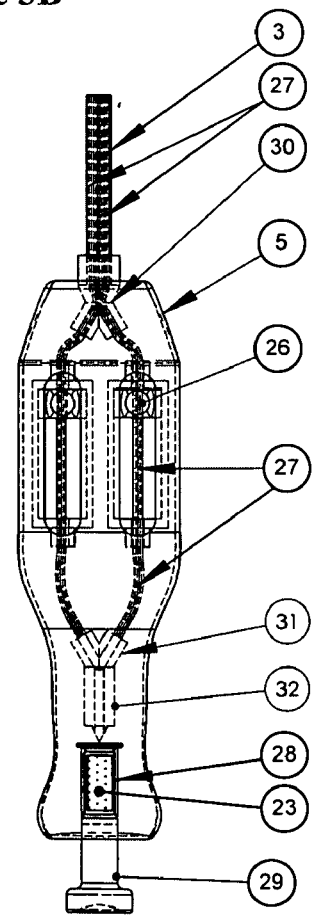
FIG. 3C shows an internal view of the delivery system from FIG. 3A.

The delivery system may comprise ease of use features as depicted in FIGS. 3A-3C, which show further exemplary embodiments of a delivery system. FIG. 3A shows an external view of a delivery device with the delivery catheters extended, wherein the delivery device comprises the following components: an atraumatic tip (1) of the introducer shaft; a balloon (8), which is depicted in the drawing as being inflated; the delivery end (7) of the delivery catheter; the shaft of the introducer (3) comprising two introducer shaft catheter channels (2), which run the interior length of the shaft and have openings for insertion of a catheter into the shaft and for the catheter to exit the shaft; that contain the delivery catheters and guide them into position; a delivery device stabilizer (4) to aid in correct placement throughout the procedure; an ergonomically designed handle (5); a slide grip (26) that is used by the operator to move the delivery catheters into position, wherein the grip has both up and down movement for extension or retraction and side to side movement for rotation of the catheter tip and wherein the position of the grip can be locked in place to prevent further motion of the catheter once the desired placement has been achieved; the shaft of the dual lumen delivery catheter (27); a occlusive material ampule (28) containing a flowable occlusive composition (23); and, a delivery plunger (29).

FIG. 3B shows an enlargement of the delivery device, as it would appear when it is proximal to the target site for delivery, where the numbered components are as described for FIG. 3A.

FIG. 3C shows internal aspects of the delivery device described in FIG. 3A, comprising the introducer shaft (3), wherein the introducer shaft has two dual lumen delivery catheters (27) disposed within it; a distal bifurcation housing (30), wherein each dual lumen catheter is directed by the distal bifurcation housing (30) to one of two slide grips (26), allowing for individual manipulation of each catheter by the operator; each catheter shaft continues from the slide grip (26) generally towards the delivery plunger (29) wherein the two catheter shafts are each attached to the occlusive material bifurcation housing (31) having a channel which directs the flowable occlusive material (23) into each of the two delivery catheters; and a component (32) capable of piercing the occlusion material ampule (28) when the plunger (29) is depressed to initiate entry of the material into the delivery catheters. Although FIGS. 3A-3C do not show a mechanism for inflation and deflation of the balloon, it should be understood that the delivery system may include such a mechanism. An embodiment of such a balloon inflation mechanism is described in the present invention, although other embodiments of this mechanism could be used therein. A method of use for this embodiment of the delivery system may be like that of the delivery system depicted in FIGS. 1A-1C, or claimed herein. For example, the system comprises introducing the delivery device transcervically with the delivery catheters contained within the introducer, each delivery catheter is moved into position and the balloon inflated, the material is delivered, and the system withdrawn.

Depicted in FIG. 4 are further exemplary embodiments of the delivery device stabilizer (4), serving a similar or additional function to that shown in FIG. 1, which allows for the fixation of the delivery system to the cervix or hold the delivery device in position during use of the delivery system of the present invention. These stabilizers may be used as a component of the delivery device described herein or may be useful for holding in position any transcervical device or instrument having a shaft, including, for example, hysteroscopes and uterine cannulas.

FIGS. 4A-4C show a method of use of one embodiment of a delivery device stabilizer which is slidable on the introducer shaft.

FIG. 4A depicts an example of a delivery device stabilizer (4) that fits into the cervical canal and expands to lock in place. Once the atraumatic tip (1) is in position at the uterine fundus (19), a delivery device stabilizer can be employed. As shown, the cervical canal (33) has a larger inner diameter than the introducer shaft (3), which allows movement of the shaft when inserted. The cervix (20) has a large enough opening to allow passage of the delivery device stabilizer (4) into the cervical canal in a collapsed or deflated state. As shown in FIG. 4B, the delivery device stabilizer (4) is moved transcervically into the canal while the introducer shaft (3) is held in place, with the atraumatic tip (1) of the introducer shaft positioned at the top of the uterine fundus (19). The collapsed expandable portion of delivery device stabilizer (4) is positioned within the cervical canal while a wider base, of sufficient size to prohibit entry into the cervix, is positioned against the external os. FIG. 4C shows the delivery device stabilizer (4) in the uterine canal, wherein the expandable portion of the delivery device stabilizer (4) is expanded or inflated. When expanded, the expansion portion of delivery device stabilizer (4) holds the delivery device stabilizer in place and prevents excessive motion of the introducer shaft (3). Although the delivery device stabilizer is shown in FIGS. 4B and 4C residing within the cervical canal, the design of this locking mechanism may also be envisioned to lie up to and even through the internal os with any portion of the length designed for expansion to enhance fixation.

FIG. 4D shows in detail an exemplary embodiment of the delivery device stabilizer (4) with an expandable portion, wherein the delivery device stabilizer mechanism may slide on the introducer shaft. The stop has a hollow core (36), which allows it to be mounted on the shaft of the introducer where it is designed to slide for proper positioning. An expandable portion (34) is mounted on a non-expandable portion (37), which is attached to a base portion (35) that is of sufficient size to prohibit passage into the cervix. The expandable portion (34) may be a balloon that is expanded with a distension medium of one or more gases or fluids, solid or semi-solid materials, to hold it in place. The expandable portion (34) may also be a mechanical device such as spiral or straight wire members that are mechanically actuated to effect expansion. The expandable portion (34) may be expanded after insertion or may be inserted in a partially or fully expanded state prior to insertion and further expanded as required after insertion into the cervix. Any means for providing an expandable portion that are known to those skilled in the art is contemplated by the present invention.

FIG. 4E illustrates an exemplary embodiment of a delivery device stabilizer with a pre-formed internal portion. The delivery device stabilizer comprises a hollow core (36) for attachment to and slidable movement relative to the introducer shaft. The stabilizer comprises a portion that fits into the cervix (38) and a base portion that remains outside the cervix (35), wherein the portion that fits inside the cervix is shaped such that it locks or wedges into or through the cervical canal and limits motion. The shape may be rounded, wedge-shaped, or have any other geometry that allows a snug fit within the cervical canal. The portion that fits inside the cervix (38) may be made from a different material than the outer portion (35) or may be made from a combination of materials. While rigid materials may be used, materials that are pliable, compressible, or expand in place such as by swelling, or some combination thereof may be preferred. The delivery device stabilizer mechanism may be designed and material selected such that the delivery device stabilizer mechanism collapses or is compressed while being pushed through the cervix and then re-expands upon placement in the target location.

FIG. 4F shows an exemplary embodiment of a delivery device stabilizer mechanism with a hollow core (36) to fit over a shaft that has a portion (38) that fits into or through the cervical canal as well as a base portion (35) that has a cup shape that conforms to the outer geometry of the cervix. FIG. 4G illustrates placement of the exemplary delivery device stabilizer mechanism of FIG. 4F, showing that the base portion with a cup shape conforms to the outer curvature of the cervix while the inner portion (38) fits within the cervical canal. The shape of the inner portion (38) may be rounded, wedge-shaped, or have any other geometry that allows a snug fit. The portion that fits inside the cervix (38) may be made from a different material than the outer portion (35) or may be made from a combination of materials. While rigid materials may be used, materials that are pliable, compressible, or expand in place such as by swelling, or combinations of such characteristics may be used. Either the internal portion (38) or the base portion (35) may be used alone or in combination as necessary to ensure appropriate fixation, stability, or both. It may be considered that the exemplary embodiments described in FIG. 4 incorporate the function of a depth stop, as shown in FIG. 1, into the design of the delivery device stabilizer (4).

FIGS. 5A and 5B show the placement of an exemplary embodiment of a delivery device stabilizer referred to as a cervical clamp. In one aspect of the present invention, the cervical clamp may be used in the delivery system that does not incorporate an additional delivery device stabilizer. In a further aspect of the present invention, the cervical clamp may be used in a delivery system that also uses one or more additional delivery device stabilizers, which may include a depth stop. FIGS. 5A and 5B show a cervical clamp (39) mounted on an introducer shaft (3), which is attached to a handle (5). The introducer shaft (3) is positioned such that the tip of the shaft (1) is positioned at the uterine fundus (19). As shown in FIG. 5A and 5B, the cervical clamp is used in combination with a delivery device stabilizer (4) incorporating a depth stop function that marks and maintains the insertion position of the atraumatic tip (1). The cervical clamp (39) is introduced into the vagina (40) in a closed or folded state, as depicted in FIG. 5A. The clamp (39) is advanced over the introducer shaft (3) until the leading edge nears the cervix (20), at which point, it is deployed and attached to the cervix (20), as depicted in FIG. 5B. The cervical clamp (39) attached to the cervix (20) functions to stabilize the introducer shaft.

FIG. 5C depicts an exemplary embodiment of a cervical clamp in which the grasping arms (42) may remain in a folded state until acted upon by a force. The cervical clamp, with a hollow core (36) to allow the clamp to move over a shaft, includes grasping arms (42), which are actuated to attach to the cervix. In this embodiment, three grasping arms are depicted. Other embodiments include devices with two, four, five, or more grasping arms. The grasping arms are positioned such that the tips of the arms (41) are in close proximity to the introducer shaft on which the cervical clamp is mounted. As depicted in FIG. 5C, tabs (43) are provided that, when squeezed by the operator of the device, cause the arms (42) and tips (41) to move outward, causing the cervical clamp to open. The clamp (39) is positioned over the cervix (20), and the tabs (43) are released, causing the clamp to fasten or attach to the cervix. The clamp is released by pressing on the tabs (43) to move the arms (42) outward, disengaging the tips (41) from the cervix. A further embodiment of the device may include a mechanism for movement of the clamp (39) relative to the shaft (3) and a mechanism for controlling the movement arms (42), wherein such mechanisms may be incorporated into the handle (S) of the delivery device.

FIG. 5D depicts a further embodiment of a cervical clamp in which the grasping arms (42) may remain in an open state until acted upon by a force. In this embodiment, four grasping arms are depicted. Other embodiments include devices with two, three, five, or more grasping arms. A compression member (44), with a hollow core (36), slides relative to the shaft of the clamp (45) and imparts a compressive force on the arms (42), deforming or moving them into a closed or folded position. To attach this embodiment to the cervix (20), the compression member (44) is advanced to compress the arms (42) to a folded state as depicted in FIG. 5A. When the clamp (39) is in place near the cervix (20), the compression member (44) is retracted to allow the arms to open. Subsequent advancement of the compression member (44) closes the arms (42) of the clamp (39), by deforming or moving the arms (42) to bring the tips (41) in to contact with the cervix (19). The compression member (44) may be advanced or retracted by mechanical means such as threads, ratchet, slider, or other mechanisms. A further embodiment of the device may include a mechanism for movement of the clamp (39) relative to the shaft (3) and a mechanism for controlling the movement of the compression member (44) incorporated into the handle (5) of the delivery system.

The tips of the arms (41) of the cervical clamp (39) may further comprise one or more grasping teeth, or may include other shapes or mechanisms for firmer or more comfortable attachment to the cervix (20). The tips (41) and arms (43) may be made from the same material or of distinct materials as required; for example, the tips may incorporate a material that is compressible and conformable to the cervix and may be designed to alter shape when in contact with the cervix to provide increased comfort or improved gripping. One aspect of the invention envisions that the tips (41) interact with the cervix (20) in such a manner that the grip strength of the clamp is sufficiently low that the patient feels little or no pain with minimal or no anesthesia while having sufficient grip strength to hold, fix, and/or stabilize the position of the introducer. The cervical clamp (39) has a cylindrical channel (36), which allows for mounting onto or sliding over the introducer shaft (3).

FIGS. 6A-6E illustrate exemplary embodiments of conduit occlusion opening or re-opening devices, or reversal devices and methods, particularly for opening or re-opening one or more occluded fallopian tubes. The example discussed herein is directed to opening occluded fallopian tubes, but this description is in no way to be seen as limiting the methods of the present invention. An introducer shaft (3) with two or more channels may be used to deliver two or more catheters (9) to the area of the fallopian tube occlusion (25). Materials or devices for opening of occlusions or reversal of occlusions may be delivered through or mounted on the delivery catheters (9). Occluded fallopian tubes may be treated simultaneously or sequentially. The delivery device allows for the opening or re-opening of two or more conduits without the need for removal and re-introduction or substantial repositioning of the device. One or more reversal methods may be used in combination to effect re-opening of the occluded conduit. It should be understood that, while depicted for use in re-opening occlusion in fallopian tubes, the methods and devices described herein may be useful for re-opening occlusions in any occluded body conduit. As used herein, the terms opening and re-opening both refer to making a non-functional conduit functional again by providing an opening through or removing an occlusion.

FIG. 6A depicts the introduction of an enzymatic, solvent, or other occlusion-degrading solution (46) to the site of the occlusion (25), such that the solution (46) degrades and removes the occlusion (25). An introducer shaft (3) is placed in position and delivery catheters (9) are advanced through the shaft through introducer shaft catheter channels (2), which run the interior length of the shaft and have openings for insertion of a catheter into the shaft and for the catheter to exit the shaft such that the catheters reach the occlusion (25). End structures (8), which may include a balloon, may be engaged, such as inflated, to limit delivery of the degrading solution to the area of occlusion (25), and may prevent retrograde flow into the uterus.

FIG. 6B shows a method of reversing an occlusion by passing a guide wire or small catheter (47) through the occlusion (25), thereby clearing the blocked fallopian tube. An introducer shaft (3) is placed in position, and one or more delivery catheters (9) are placed through the shaft through introducer shaft catheter channels (2), which run the interior length of the shaft and have openings for insertion of a catheter into the shaft and for the catheter to exit the shaft such that the catheters reach the occlusion (25) in one or both of the fallopian tubes. A guide wire (47) or a small catheter (47) is passed through the delivery catheter (9) and advanced across the occlusion (25). The occlusion is removed or cannulated, thereby reopening the fallopian tube. Material for use in the small catheter may be sufficiently stiff to allow for movement across and through the occlusive material or tissue.

As depicted in FIG. 6C, one or more catheters (9) with attached balloon (48) may be placed through an introducer shaft (3) through introducer shaft catheter channels (2), which run the interior length of the shaft and have openings for insertion of a catheter into the shaft and for the catheter to exit the shaft such that the catheters can be advanced such that the balloon (48) is within the area of occlusion (25). Inflation of the balloon may effect clearing of the occlusion. The catheter with attached balloon may pass directly through the introducer shaft (3) to reach the occlusion (25) or may pass through a larger catheter (not depicted) that passes through the introducer shaft (3) to the area of the occlusion (25). The balloon may be further used to effect delivery of a stent or other structure that maintains the re-opened channel after reversal of the occlusion.

FIG. 6D depicts a method of clearing fallopian tube occlusions by using a cutting or debriding mechanism. The cutting mechanism (49) may comprise or be similar to, for example, a device for atherectomy (directional coronary atherectomy), rotoblation (percutaneous transluminal rotational atherectomy), or a cutting balloon. One or more delivery catheters (9) are passed through an introducer shaft (3) through introducer shaft catheter channels (2), which run the interior length of the shaft and have openings for insertion of a catheter into the shaft and for the catheter to exit the shaft such that the catheters can be advanced to the vicinity of the occluded region (25). A cutting device (49) is advanced through the delivery catheter (9) to the occluded region (25). The cutting device is used to remove the occlusion (25), thereby reopening the fallopian tube.

FIG. 6E depicts a method of clearing an occlusion by using an energy-producing device (50). Ultrasound, RF energy, microwave, laser, radiation, heat, or other energy sources may be used. An introducer shaft (3) is placed, and one or more delivery catheters (9) are inserted through the introducer shaft through introducer shaft catheter channels (2), which run the interior length of the shaft and have openings for insertion of a catheter into the shaft and for the catheter to exit the shaft so that the catheters can be provided to the area of the occlusion (25). An energy-producing device (50) mounted on a catheter or wire is passed through the introducing catheter (9) and into the occluded region (25). The occluded region is subjected to energy from the energy source, which removes the occlusive material and clears the occlusion.

FIG. 6F depicts a uterus that has been subjected to one or more of the methods depicted in FIGS. 6A, 6B, 6C, 6D, and 6E. After treatment, the occlusion has been re-opened or removed, leaving patent fallopian tubes (51).

The delivery systems of the present invention comprise means for introducing delivery devices into the body, means for providing occlusive material such as reservoirs and pumps, devices for in situ delivery of compositions comprising occlusive materials, means for polymerizing or coagulating the occlusive materials, including mechanical, biological or chemical means; means for visualization of procedures, pre- and post-procedural compositions and methods of treatment, means and compositions for supporting or inducing tissue ingrowth or degradation of the occlusive material, and means for re-opening of the occluded conduit.

The present invention further comprises methods for occluding fallopian tubes that are useful for providing female sterilization. It is well known in the art that a primary cause of naturally occurring infertility in females is blockage of the oviducts from the ovary to the uterus. Females having this natural condition normally do not even realize it exists and do not suffer any adverse side effects besides being infertile. Moreover, the condition can often be successfully reversed, thus restoring the ability to bear children. Based upon the observations of naturally occurring oviductal occlusion, the creation of tubal occlusions by external intervention has arisen as a potential means of effecting female sterilization.

Aspects of the present invention comprise a delivery system, compositions comprising one or more occlusive materials, and a method for tubal occlusion and more particularly occlusion of the fallopian tubes of a female mammal for the purpose of reversible sterilization. In one aspect of the invention, the delivery device is inserted either directly or through an introducer sheath and positioned to reach the area in which the occlusion is desired while the operator non-invasively visualizes the delivery to ensure correct placement. Once in place, the operator instills the occlusive agent through a channel in the delivery catheter, creating the occlusion. The delivery device is then withdrawn, leaving the occlusion in place. Over time, fibrous tissue grows into the material as it resorbs, leaving an occlusion fashioned of the patient's own tissue. The delivery system may be used to deliver an agent, such as a device or composition, to reverse the occlusion, and methods for re-opening the occlusion are described.

As envisioned for female sterilization, a delivery system comprises a transcervical introducer sheath generally made of a standard medical-grade metal or plastic such as stainless steel, nylon, PTFE, or polyurethane, which may be naturally sonolucent or may require enhancement of ultrasound visibility by coating with a sonolucent material or otherwise modifying the material. The sheath may comprise an atraumatic tip to allow for comfortable placement and, combined with selection of a suitably flexible material, to prevent damage to the uterine wall. The introducer shaft has sufficient diameter to allow for introduction of other components of the delivery system. The introducer may contain one, two or more channels that guide catheters into position, for example delivery catheters for delivery of occlusive materials. The introducer may include a mechanism to modify the angle of the introducer relative to the surrounding tissues, such as the cervix or uterus, to allow for a better fit to the anatomy of the individual patient, including such individual variations as ante- or retroverted/ante- or retroflexed uterus. Modified versions of the introducer may allow for uses other than for the occlusion of the fallopian tube(s), such as the localized delivery of contrast media for confirmation of tubal patency or the delivery to or removal from the fallopian tube(s) of other material or devices for diagnosis, treatment, or examination of the tube, including the delivery of systems for re-opening an occlusion. One aspect of the introducer sheath is that it can be visualized using noninvasive techniques such as ultrasound. Visualization may be used to guide accurate placement and to ensure that the tip of the device does not penetrate the uterine wall. A delivery device stabilizer may be included to ensure that accurate placement is maintained throughout the procedure. The delivery device stabilizer may comprise or include a means to fix or hold the introducer in place, such as a mechanism or device to attach or hold the introducer within the cervix or to otherwise maintain the device in the desired position, minimizing risk to the patient and allowing the operator greater flexibility to carry out other aspects of the procedure. Fixation may be accomplished through physical means such as clamping, suction, wedging, inflation, or by other means that maintain the device in the desired position.

A delivery system of the present invention comprises a device that can be configured in a collapsed, retracted, or folded form for insertion through the cervix, which may comprise an introducer sheath. After introduction, the device is positioned allowing an atraumatic tip containing a single or multiple holes at the tip of the device to reach the desired location, such as within the cornual aspect of the uterus at or near the ostium of a fallopian tube. The present invention comprises a device that has at least one end of a delivery catheter with an opening that is placed within the cornual aspect of the uterus at or near the ostium of a fallopian tube. In one embodiment, the delivery device comprises two delivery catheters, with each catheter having its delivery opening positioned simultaneously or sequentially at the ostia of both fallopian tubes. In another embodiment, such a device may be shaped like a Y, a T, or an arrow wherein the two delivery ends of the shape are positioned within the uterine cornua at or near the ostia. The delivery system may utilize existing catheter-based technology, for example, balloon catheters, and may incorporate standard materials such as Pebax, nylon, PTFE, polyurethane, vinyl, polyethylene, ionomer, polyamide, polyethylene terephthalate, and other materials. These materials may be naturally sonolucent or may be modified to enhance their ultrasound visibility, such as by coating or the inclusion of air bubbles within the material. Embodiments of the present invention may include a means for controlled flexion or rotation of the delivery system, which may aid in positioning one or more ends at the desired anatomic location. The catheters may be designed with one or more curves that ensure that the tip is guided to the uterine cornua. Such curves may be either pre-formed to suit a majority of female reproductive anatomies or may be selected based on the individual anatomy of a single female patient.

The present invention comprises methods for occlusion of fallopian tubes comprising delivery of devices, such that the methods incorporate intra-procedure non-invasive visualization without hysteroscopy, and positioning of the delivery ends of a delivery device within the uterine cornua at or near the ostia of both fallopian tubes without the need for removal and reintroduction of instrumentation. Embodiments of the present invention comprise delivery devices that are sized appropriately for a general population of patients and also comprise delivery devices that are custom-fitted and individually tailored to meet individual patient anatomical needs. Delivery devices taught in the prior art, such as U.S. Pat. Nos. 5,746,769, 6,145,505, 6,176,240, 6,476,070, 6,538,026, 6,634,361, 6,679,266, and 6,684,384, 5,954,715, 6,068,626, 6,309,384, 6,346,102, and 6,526,979 do not consider individual patient anatomy, may require the use of a hysteroscope for direct visualization, and necessitate cannulation of each tube sequentially, with the need to reposition, withdraw and reinsert the device, enhancing the technical difficulty of the procedure and consequently the inherent risk of failure.

One aspect of this invention contemplates the use of pre-procedure imaging, such as by ultrasound, to allow for selection or adjustment of lengths and angles of the deployed delivery device and selection of appropriate delivery device stabilizer to accommodate individual patient anatomy. This pre-procedure imaging is used to rule out anomalies that may preclude use of the system and may be used to determine the uterine width between the fallopian tubes to select the correct size delivery system or to adjust the angle or shape of each of the two delivery ends such that each would be properly located within the uterine cornua at or near the ostium of a tube on deployment. Imaging may also elucidate the size and shape of the cervical os and canal, guiding selection of size and shape of delivery device stabilizer or spacer. Alternatively, one of a set of predetermined sizes of the delivery system could be selected based on the pre-procedure imaging information. The ability to adjust placement of the delivery ends or tips, including the angle and length for each individual end or in combination, during the procedure based on tactile feedback, imaging, or both tactile and imaging information is also contemplated. Other pre-procedure methods include the use of hormonal medications to control estrogen/progesterone cycle changes or prevent placement of the device during pregnancy and the use of pre-operative medications such as anti-infective or immune response therapies.

The present invention further comprises post-procedure methods and compositions. Post-procedure methods may comprise, for example, ultrasound or X-ray visualization, to allow for confirmation that the occlusive material continues to provide an occlusion over time. Post-procedure methods and compositions may further comprise the use of hormonal agents to prohibit menstrual shedding of the endometrium is also contemplated to minimize the risk of expulsion for a period of time, for example to allow for a period of time for resorption of the occlusive material and tissue ingrowth. For example, use of a long-acting hormonal medication such as an injectable medroxyprogesterone acetate depot may serve the function of both the pre- and post-operative hormonal therapy without the need for reliance on patient compliance. Post-operative methods and compositions may further comprise antibiotic or steroidal compositions.

Methods of the present invention comprise visualization of one or more steps of the methods. Visualization of the insertion, placement of the device, and release of the occlusive composition are included in methods for providing the occlusive material. Visualization of the occluded region, removal of the occlusive material, reopening of the conduit and testing for return of functionality of the conduit are included in methods for reversing the occlusion of the conduit. Such visualization methods are known to those skilled in the art. U.S. Pat. Nos. 4,731,052 and 4,824,434 teach that ultrasound may be used for visualization of internal structures. The compositions and devices of the present invention comprise materials that allow for visualization, such as by ultrasound, during the procedure to ensure appropriate patient selection and device placement and localization, and for post-application monitoring to confirm appropriate material placement and the presence of an occlusion.

Once the delivery device is appropriately placed, the occlusive material is introduced through the delivery device to create the occlusion of the fallopian tubes. In one aspect of the invention, the delivery device has individual channels in the shaft of the introducer, with capability to provide a delivery end or tip directed toward the opening of a fallopian tube. An aspect of the invention allows for the simultaneous or sequential delivery of occlusive material to the fallopian tubes without the need to withdraw and reinsert or substantially reposition the device. The occlusive material is delivered by actions of the operator manually or automatically once the device is in position. One aspect of the invention contemplates the occlusive material is visualizable by non-invasive imaging such as ultrasound. Materials may be naturally sonolucent or may be modified to have enhanced sonolucency by the introduction of materials or bubbles such as microbubbles of air or gas. These microbubbles may be present within the material prior to attachment to the delivery system or may be introduced into the material during the delivery process, such as through the use of a cavitation mechanism.

It is contemplated that the methods taught herein are effective with one application of occlusive material to at least one conduit, though the methods comprise at least one application to at least one conduit. Embodiments also comprise one or more applications of occlusive material to at least one conduit during one delivery cycle. For example, once the delivery device is in place in the uterus, with at least one end of the device at the site or sites to be occluded, occlusive material may be applied once, and then, without removal, one or more other applications of occlusive material are performed. Alternatively, occlusive materials may be placed at the site or sites for occlusion over multiple treatments. For each treatment, the delivery device would be inserted and removed. Such multiple applications may occur on consecutive days of insertion and removal or the days of insertion and removal may be interspersed with days of no applications of occlusive material. Such treatment regimens may be designed with individual patient needs taken into account by those skilled in the art, such as the treating physicians. Such treatment regimens may utilize the same or different occlusive compositions at each application.

The occlusive compositions include natural or synthetic materials. Natural materials include those found in animals or plants and not necessarily in the species in which they are used. Synthetic materials include any materials that can be made by humans or machines in laboratory or industrial settings. The compositions may comprise materials that are initially mostly fluid that polymerize in situ to become solid materials, may comprise solid materials that may or may not change properties such as flexibility, once placed at the site or sites for occlusion, may comprise a mixture of fluids with gas, solid articles or both, dispersed therein. The occlusive material compositions may be a pre-formed shaped material that is released by the device once one or more delivery ends are in position, and the compositions may comprise occlusive material that starts as a liquid or semi-solid that cures in situ. The compositions of the present invention may include solid structures such a stents, rods, pellets, beads, and other tissue bulking agents that provide a solid structure to the occlusion formed at the site or sites. Compositions of the present invention may also combine pre-formed structures, such as spheres or particles, with material that starts as a liquid or semi-solid and cures in situ, entrapping the preformed structures.

One aspect of the present invention comprises an occluding composition comprising a liquid that is mixed prior to delivery or does not require pre-mixing such as the single liquid composition, is ultrasound visible, and cures upon delivery into and through the tubal ostia within 5 cm of the ostium to provide mechanical blockage and is at least 75% resorbed at a range of between about 30 to about 365 days. In one embodiment, the occluding composition is not hydrophilic and does not swell in the presence of fluids in the environment. In another aspect, the occlusive composition forming the occlusion may aid in the initiation or stimulation of tissue growth into the occluded site, wherein the occlusion is replaced by tissue that maintains the occlusion after resorption of the occlusion material. In another aspect, an embodiment of the invention contemplates use of an occlusive material that has a functional lifespan wherein for a period of time it forms the physical occlusion or blockage of the lumen, and after period of time, the occlusive material is gone, having been resorbed or degraded, but is not replaced by tissue ingrowth, so that the lumen is again open and functional.

In a further aspect of the present invention, the occlusive material comprises a two component liquid comprising a resorbable polymer solution component and a liquid cyanoacrylate tissue adhesive component. The resorbable polymer is a polyester polymer selected from polylactide, polyglycolide or polycaprolactone, or a polyester copolymer selected from poly(lactide/glycolide) acid (PLGA) or poly (lactid-co-ϵ-caprolactone) (PLCL). The cyanoacrylate tissue adhesive component comprises any of a number of biocompatible alkyl- or alkoxyalkyl-2-cyanoacrylates such as n-butyl-2-cyanoacrylate or 2-methoxybutyl-2-cyanoacrylate. The two component liquids are mixed prior to entry in the catheters for delivery. In curing, the cyanoacrylate homopolymerizes and entraps the polyester polymers or copolymers. The cyanoacrylate adheres to the lumen wall to anchor the occlusion in place.

A single liquid composition is also contemplated. The single liquid composition comprises a liquid tissue adhesive, such as a cyanoacrylate with a nano- or micro-particulate material, which may be made from resorbable polyesters. In one aspect of the invention, the particles are capable of visualization by ultrasound. The particles and tissue adhesive are combined prior to delivery to the target site. The composition cures by the homopolymerization of the tissue adhesive, entrapping the particles, and anchors the occlusion in the lumen by adhesion to the lumen wall.

The resorbable nature of the occluding composition and the proximity of the occlusion to the ostia, extending over a limited length of the fallopian tube, may allow for ease in the reversibility of the contraceptive method. As the occlusive implanted composition is resorbed, there is ingrowth of tissue that maintains the occlusion. The tissue occlusion so formed can be recanalized to provide an open conduit for fertilization without the need for surgical removal and reapposition of the tube across the area of the occlusion.

A wide variety of materials are known in the art that can be used to form the conduit occlusions of the present invention, such as oviduct occlusions. U.S. Pat. No. Re. 29,345 teaches the use of silastic that is partially pre-formed and partially in situ cured. U.S. Pat. No. 4,185,618 teaches the use of a gel-forming carrier substance that holds in place a tissue fibrosis-promoting material. U.S. Pat. Nos. 4,365,621 and 4,509,504 describe the use of a swelling material that is inert and permanent. U.S. Pat. No. 6,096,052 describes the use of a mesh-based material that supports fibrous tissue ingrowth. U.S. Pat. No. 4,700,701 describes the use of a resorbable plug in combination with physical and/or chemical means of inducing a scarring reaction. U.S. Pat. No. 5,989,580 incorporates the use of a biocompatible, non-degradable implanted polymer of several types that can be removed by dissolution. U.S. Pat. No. 6,605,294 teaches the use of absorbable polymers, pre-shaped with at least one rod-shaped portion, to occlude fallopian tubes. U.S. Pat. No. 5,894,022 teaches using a composition that may form a degradable mesh. U.S. Pat. Nos. 6,371,975, 6,458,147, and 6,743,248 teach the use of a polyethylene glycol and protein composition for the occlusion of vascular access puncture sites. The present invention comprises these and other occlusive compositions for blocking a conduit that may be introduced using the delivery devices of the current invention.

One aspect of the occlusive compositions of the current invention comprises a resorbable material capable of providing an initial mechanical blockage and initiating or supporting the tissue ingrowth necessary to create the occlusion and/or an adhesive composition that maintains the position of the material during curing and the initial phase of tissue ingrowth. U.S. Pat. Nos. 4,359,454, 6,476,070, and 6,538,026 teach the use of cyanoacrylate, and in particular a composition containing either n-methyl or n-hexyl cyanoacrylate, as a resorbable, yet scar-promoting, material. Other patents teach compositions of polymerizable monomers, such as cyanoacrylates, alone or in combination with other materials, such compositions that may be useful as occlusive agents or adhesives in the present invention and/or as resorbable materials capable of initiating or supporting tissue ingrowth to form a permanent adhesion. These include U.S. Pat. Nos. 5,328,687, 5,350,798, 6,010,714, 6,143,352, 6,174,919, 6,299,631, 6,306,243, 6,433,096, 6,455,064, 6,476,070, 6,538,026, 6,579,469, 6,605,667, 6,607,631, 6,620,846, and 6,723,144.

A further aspect of the current invention includes materials that are delivered in a solid or non-solid form which may be used to deliver or adhere materials that may be useful in promoting or forming occlusions or which may be useful in forming occlusions in and of themselves whereas such material may be resorbable or permanent. Such materials include dry compositions that hydrate and form crosslinked hydrogels, as taught by U.S. Pat. No. 6,703,047. U.S. Pat. Nos. 5,612,052, 5,714,159, and 6,413,539 teach self-solvating polyester copolymers that form hydrogels upon contact with body fluids. U.S. Pat. No. 4,804,691 teaches compositions of hydroxyl-terminated polyesters crosslinked with diisocyanate. U.S. Pat. No. 6,723,781 teaches crosslinked, dehydrated hydrogels. Hyaluronic acid based hydrogels are taught in U.S. Pat. Nos. 5,866,554 and 6,037,331. Two part hydrogels are taught in U.S. Pat. No. 6,514,534. Crosslinked bioadhesive polymers are taught in U.S. Pat. Nos. 6,297,337 and 6,514,535. Thermosensitive biodegradable polymers are taught in U.S. Pat. No. 5,702,717.

The present invention comprises compositions that form an occlusion in a conduit, wherein the occluding material is resorbed or biodegraded by the body in a range from at least about 20% to about 100%, or in a range from at least about 20% to about 80%, from a range of at least about 20% and about 60%, from a range of at least about 30% to about 50%, from a range of at least about 30% to about 80%, from a range of about 70% to about 100%, and from a range of about 40% to about 100%. Such resorption may occur substantially over a period of time from about 30 days to 365 days, from about 30 days to 180 days, from about 30 days to 90 days, from about 60 days to 365 days, from 60 days to 180 days, or from about 90 days to 365 days. A composition comprises a material that is resorbed or biodegraded by the body in a range of at least about 20% to substantially 100% in a period of time of about 30 days to 365 days, where the initial mechanical occlusion formed by the material is maintained thereafter by the tissue that grows into the site.

The present invention contemplates use of an in situ curable material, which lowers the risk of expulsion by allowing the material to conform and adhere to the walls of the conduit, or specifically the uterus and/or fallopian tube. Compositions capable of in situ curing preferably comprise a material that is flowable at a temperature outside physiologic limits but curable at physiologic temperatures such as those taught by U.S. Pat. Nos. 5,469,867 and 5,826,584. High viscosity liquids capable of delivering and maintaining materials in place that are useful for the present invention are taught in U.S. Pat. Nos. 5,747,058, 5,968,542, and 6,413,536. Alternatively, the material may cure on contact with the tissue environment as described in U.S. Pat. Nos. 4,359,454, 6,476,070, and 6,538,026; on contact with a curing agent as described by U.S. Pat. Nos. 5,278,202 and 5,340,849; or on dissipation of the solvent as described by U.S. Pat. Nos. 4,938,763, 5,278,201, 5,324,519, 5,487,897, 5,599,552, 5,599,552, 5,632,727, 5,702,716, 5,728,201, 5,733,950, 5,736,152, 5,739,176, 5,744,153, 5,759,563, 5,780,044, 5,792,469, 5,888,533, 5,990,194, 6,120,789, 6,130,200, 6,395,293, 6,461,631, 6,528,080, and Re. 37,950 as well as world-wide patent numbers WO 97/42987, WO 99/47073, and WO 00/24374.

The present invention comprises use of compositions made from a combination of more than one material to form the occlusion, particularly compositions that comprise materials that cure or polymerize by differing mechanisms. For example, the compositions may comprise a combination of two materials, one of which cures or polymerizes because an activating agent is present and the other cures, polymerizes or solidifies, all of which are interchangeable terms, because of the pH of the environment in which it is placed. Components of the mixture may serve different or overlapping roles; for example, a tissue adhesive component may primarily serve to minimize expulsion of the implant while tissue in-growth is occurring, while another component may primarily initiate or support the tissue growth. The tissue adhesive component may be selected from the group of materials containing the cyanoacrylates, polyacrylic acids, polyethylene glycols, modified polyethylene glycols, thrombin, collagen, collagen-based adhesives, fibrin, fibrin glue compositions, gelatin-resorcinol-formaldehyde-glutaraldehye (GRFG) glue, autologous blood in combination with collagen and/or thrombin, crosslinked albumin adhesives, modified glycosaminoglycans, poly(N-isopropylacrylamide)-based adhesives, alginates, chitosan, and gelatin, crosslinked with carbodiimide or genepin, among others, in a proportion of the overall composition from about 5% to 50%, from about 5% to 25%, from about 10% to 50%, or from about 10% to 25%. The material added primarily for the initiation or support of tissue ingrowth may be chosen from the group consisting of solid or solvated resorbable polymers, including the resorbable polyesters or their copolymers. The tissue ingrowth component, including or excluding the presence of solvent, may comprise from about 20% to 80%, from about 50% to 80%, from about 40 to 70%, or from about 50% to 90% of the overall composition. When a copolymer is used the percentage of each polymer within the copolymer will be from about 25% to 75%.

Additional components may be included to stabilize the overall mixture or to control the viscosity, curing time, resorption timeframe, plasticity, or to enhance visualization of the material. Such agents may include: polymerization inhibitors and stabilizers including, for example sulfonic acid, lactic acid, acetic acid, sulfur dioxide, lactone, boron trifluoride, hydroquinone, hydroquinone monomethyl ether, catechol, pyrogallol, benzoquinone, 2-hydroxybenzoquinone, p-methoxy phenol, t-butyl catechol, organic acid, butylated hydroxyl anisole, butylated hydroxyl toluene, t-butyl hydroquinone, alkyl sulfate, alkyl sulfite, 3-sulfolene, alkylsulfone, alkyl sulfoxide, mercaptan, and alkyl sulfide; emulsifying agents such as polyvinyl alcohol; echogenic agents such as microbubbles of air or gas, microparticles or spheres of crosslinked albumin with entrapped air or gas (Albunex), sonicated albumin, gelatin-encapsulated air or gas bubbles, nanoparticles, microparticles, spheres, or microcapsules of resorbable polyesters or other resorbable materials with entrapped air or gas, particles of other materials with entrapped air or gas; contrast agents such as gold particles; viscosity-modifying materials such as crosslinked cyanoacrylate, polylactic acid, polyglycolic acid, lactic-glycolic acid copolymers, polycaprolactone, lactic acid-caprolactone copolymers, poly-3-hydroxybutyric acid, poly-orthoesters, polyalkyl acrylates, copolymers of alkylacrylate and vinyl acetate, polyalkyl methacrylates, and copolymers of alkyl methacrylates and butadiene; and plasticizers such as dioctyl phthalate, dimethyl sebacate, trethyl phosphate, tri(2-ethylhexy)phosphate, tri(p-cresyl)phosphate, glyceryl triacetate, glyceryl tributyrate, diethyl sebacate, dioctyl adipate, isopropyl myristate, butyl stearate, lauric acid, dibutyl phthalate, trioctyl trimellitate, and dioctyl glutarate. The composition may further contain colorants such as dyes and pigments.

The total amount of these agents may comprise from about 0.1% to 10%, from 1% to 10%, or from 5% to 20% of the overall composition.

The combination of two or more materials that cure by different mechanisms, including contact with tissue or the appropriate curing environment for example, conditions such as aqueous, ionic, temperature, or pH, chemical crosslinking, or solvent dissipation, among others, is contemplated by the current invention. The combination of one or more materials that cure by one or more mechanisms combined with one or materials that are pre-cured or pre-formed into particles, spheres, or other structures, is also contemplated by the current invention.

The present invention contemplates the use of pre-formed solid materials such as particles, spheres, capsules, or the like, in combination with a liquid or semi-solid material. The pre-formed solids may comprise degradable or resorbable materials and may have enhanced ultrasound visibility or may serve to enhance ultrasound visibility of the composite occlusive material. The particles as contemplated may be nanoparticles of an average size ranging from about 100 to 2000 nanometers, about 100 to 1000 nanometers, about 250 to 2000 nanometers, or about 500 to 2000 nanometers in diameter. Particles may also be microparticles with an average size ranging from about 0.1 to 1000 micrometers, about 0.1 to 250 micrometers, about 1 to 500 micrometers, about 50-500 micrometers, about 100-750 micrometers, or about 250 to 1000 micrometers. The liquid or semisolid material acts as a transport medium for the pre-formed solids and then cures in situ, entrapping the solids. The particles may be coated with or contained within a material that enhances their miscibility with the liquid or semi-solid material or minimizes the tendency of the particles to promote the premature curing of the liquid or semi-solid material prior to delivery. Coating materials may include extremely low moisture content formulations of the particulate constituent materials or other polymers or copolymers containing, for example, caprolactone, poly-β-hydroxybutyrate, delta-valerolactone, as well as polyvinylpyrrolidone, polyamides, gelatin, albumin, proteins, collagen, poly(orthoesters), poly(anhydrides), poly(α-cyanoacrylates), poly(dihydropyrans), poly(acetals), poly(phosphazenes), poly(urethanes), poly(dioxinones), cellulose, and starches. The following patents and U.S. patent applications teach manufacturing methods for creating echogenic particles for use in ultrasound contrast agents: U.S. Pat. Nos. 5,352,436; 5,562,099; 5,487,390; 5,955,143; 2004/0161384; 2004/0258761; and 2004/0258769. Particles made by these methods are contemplated by the present invention.

The present invention also comprises methods for sequential applications of the same or different materials. For example, a composition of the occluding material that functions as the in situ curable material may be placed in the site or sites, and an adhesive composition may be applied separately either before or after the curable material so as to fix the implanted material in place, thus lowering the risk of expulsion. The in situ curable materials may cure or solidify in the native environment of the fallopian tube, or the curing may require the presence of an energy source, such as light, heat, other electromagnetic waves, sound waves, or microwaves or the presence of an initiator and/or accelerator for curing. The additional energy sources may be provided by the delivery device or another introductory vehicle or by sources outside the body.

The end structure of a delivery catheter may have alternative shapes that aid in maintaining the end at the site, aid in delivery of occlusive material, aid in removal of the delivery device from the site, aid in localizing the occlusion and other shapes and designs for functions by the end. For example, a delivery catheter used for occluding the fallopian tubes in a mammal, having an end that is placed within the uterine cornua at or near the tubal ostia, may have end structures that comprise a shape that aids in delivery of the occlusive material, for example by maintaining it in position. This end structure may function to guide tip placement of the delivery system or anchor the arm ending to and/or cover the ostium of the tube and may take the form of a nozzle, cup, or balloon. A nozzle, cup or balloon is useful for preventing leakage of compositions of in situ curable material away from the implantation site. Preferably, the end structures do not adhere to the implantable material although the use of an absorbable, detachable end structure that may adhere to the implantable material and be left in place after removal of the remainder of the delivery system is also contemplated. Using a device having a structure that conforms to the shape of the uterine cornua, maintaining localized delivery to at least one ostia eliminates the need to cannulate into the fallopian tube.

The present invention comprises methods for female sterilization wherein the delivery device is not inserted into the fallopian tube and in which the occlusive material is introduced within the uterine cornua at or near the tubal ostia affecting portions of the endometrium and/or tubal epithelium. The extent of the occlusion such as the portion of the uterine cornua and fallopian tube blocked by the occlusive material, may be controlled by modification of the curing time, viscosity, and amount of material delivered. The current invention comprises methods for effective blockage of a conduit, such as a fallopian tube, by occluding a minimal portion of the fallopian tube. Such occlusion may block a conduit for less than 1.0 mm of the length of the conduit, for less than 1 cm of the length of the conduit, for less than 3 cm of the length of the conduit, or for less than 5 cm of the length of the conduit. For example, in occluding a fallopian tube, an embodiment of the present invention comprises methods of application of an occluding material such that no more than 5 cm of the fallopian tube is occluded. In affecting this length of tube, the anatomical areas of the fallopian tube targeted for occlusion include the areas within the uterine wall (the interstitial segment) and early portions of the isthmic section. The present invention may not be dependent on the length, width or depth of the solidified occluding material, and the extent of the solidified occluding material may be dependent on whether subsequent reversal of the occlusion is desired. If reversal of the occlusion is contemplated at the time of occluding, a minimal amount of occlusion may be achieved, thus allowing for more ease in reversing the occlusion and opening the conduit.

In one method of delivery of the occlusive material, pressure generated in the lumen of the delivery system forces the occlusive material through the delivery device, including at least one opening in at least one delivery end, out of the device and into the area to be blocked. Once the occlusive material has been delivered, the delivery device is removed in whole or in part from the patient (the end structure may be detachable and fashioned from a resorbable material designed to be left in place). For example, once the occlusive material is delivered to the site or the occlusive material cures in situ, the delivery device can be collapsed, re-folded, re-sheathed, or directly removed in one or more pieces from the patient.

The compositions of the present invention comprise occlusive materials and may further comprise one or more agents that are capable of providing other functions, including but not limited to, a curable carrier for the occlusive material, allowing for controlled release of a substance, enhancing the ability of the occlusive material to cause fibrosis or inhibit contraception. Quinacrine is well established to create scarring of the tubal epithelium and cause tubal blockage. In combination with the occlusive material, low dosages of quinacrine or other sclerotic agents, such as tetracycline, may assist in creation of the fibrous tissue blockage. The compositions of the present invention comprise fibrous tissue growth promoting agents such as growth factors or pro-inflammatory reagents that are known to those skilled in the art. U.S. Pat. No. 3,803,308 teaches that the instillation of copper or zinc salts alone into the uterus inhibits contraception. Current copper intrauterine devices have incorporated this concept. The present invention comprises compositions comprising copper salts or other metallic elements in addition to the occlusive material. Inclusion of hormonal contraceptives within the occlusive material to limit further the risk of pregnancy during the timeframe of tissue ingrowth is contemplated.

The present invention comprises methods for using energy-delivering devices to initiate or completely form an occlusion. Such methods comprise activities at the site of the placement of the occlusive materials to aid in the formation of tissue growth and/or biodegradation of the occlusive material. Such activities include, but are not limited to, use of cautery methods, bipolar coagulating current, a high frequency generator to produce a tissue damaging current, and use of laser, light, microwave, and radiofrequency energy. Devices for providing such activities and uses thereof are taught in U.S. Pat. Nos. 4,700,701; 5,095,917; 5,474,089; 5,954,715; and 6,485,486.

The present invention also comprises delivery systems, methods and devices for removing at least one occlusion at the occluded site. As used herein, the term reversing the occluded site, means making the conduit capable of transporting again. Making the conduit capable of transporting can include, but is not limited to, removal of the original occluding material, creating a new lumen through the occluded site, such as forming a channel through the occluding material or the in-grown tissue at the occluded site, or by-passing the occluded site. The methods of the present invention comprise delivery of devices that place permanent plugs within one or more conduits, simultaneously or sequentially, wherein such plugs are structured such that a device of the present invention can be used to remove the plugs at a later time. Structures for such plugs are taught U.S. Pat. No. Re. 29,345. Such plugs are not resorbable or biodegradable by bodily actions and thus incorporate means for anchoring the plugs within the conduit. The occlusion may be removed from the conduit by destruction of the occluding material. For example, shockwaves can be used to shatter the material, similar to that used in lithotripsy methods, and the material is expelled from the conduit. Chemical or biological means, such as instillation of solvents or enzymes, can be used to disintegrate the occlusion. Removal devices of the present invention can be used to affect one or both fallopian tubes that have occluding material therein, by physical removal of plugs, provision of materials that recanalize the occluding site, or that mechanically form a new channel through or around the occluded site. The device may also deliver a stent or other device to ensure that the new channel remains open. U.S. Pat. Nos. 4,983,177; 5,989,580; 4,664,112 and others teach methods for reversibility of occluded sites. In methods for reversing the blockage of fallopian tubes, the present invention contemplates systems, methods and devices that are capable of reversing the occlusion in each fallopian tube under non-invasive visualization and without removal and reinsertion or the need to reposition substantially the delivery device until both tubes are unblocked. Although it may be desirable to open the tubes one at a time, the ability to reach both tubes under non-invasive visualization and without the withdrawal and reintroduction of instrumentation represents an advantage over the prior art.

In one aspect of the present invention in which a partially or fully resorbable material is used to cause occlusion of a conduit, minimal or no permanent foreign body remains in position. In fallopian tube occlusion, the occlusion is located at or near the ostium of the tube, making non-surgical access simple. A catheter with a working head for the removal of an occlusion in a vessel or other body passageway can be used with the delivery device. A method for reversal of such blocked tubes incorporates the use of a catheter-based delivery system similar to that used for the introduction of the occlusive material. In this aspect of the invention, the channel or channels of the delivery device are used for the introduction of a stiff or cutting catheter or a catheter for instillation of a dissolution medium (e.g., enzyme or solvent) that recanalizes the blocked section(s) of the tube. A stent or other device to maintain the opening may be placed through the delivery device as well.

In general, the present invention comprises methods for occluding at least one conduit in a human or animal body, comprising, providing a delivery system capable of delivering an effective amount of a composition comprising an occlusive material, wherein the delivery system comprises a delivery device comprising at least an introducer shaft for providing at least two catheters; two catheters, each comprising an end structure on a delivery end and attachment means on a proximal end, a composition comprising an occlusive material, and means for providing the composition comprising an occlusive material into and through the catheters; delivering an effective amount of the composition comprising an occlusive material at or near the target site such that the material occludes the lumen of the conduit; and occluding the conduit with the composition comprising an occlusive material within the lumen of the conduit. Means for providing the delivery composition include, but are not limited to, syringes and pressure systems, pumps, containers with plungers to force material into the catheters, or other methods and devices for moving flowable material through a catheter or tube. The methods further comprise opening conduits, whether the conduit is occluded by methods of the present invention or by other methods or processes, including natural and synthetic or medical processes. The methods may comprise occluding two conduits without removal and re-introduction or substantial repositioning of the introducer shaft. Such a method may be used to treat fallopian tubes of a mammal, and provides methods of contraception.

The compositions used in the methods of the present invention comprising the occlusive material may be mixed prior to delivery to the lumen. The compositions may comprise a liquid tissue adhesive and a solvated polymer, wherein the composition cures in situ. The composition comprising the occlusive material may be ultrasound visible. The ultrasound visible material may comprise microbubbles of air or gas or microparticles of a material that entrap air or gas. Compositions of the present invention comprise compositions wherein the liquid tissue adhesive is cyanoacrylate, polyacrylic acids, polyethylene glycols, modified polyethylene glycols, thrombin, collagen, collagen-based adhesives, fibrin, fibrin glue compositions, gelatin-resorcinol-formaldehyde-glutaraldehyde (GRFG) glue, autologous blood in combination with collagen or thrombin, crosslinked albumin adhesives, modified glycosaminiglycans, poly(N-isopropylacrylamide)-based adhesives, alginates, or chitosan or gelatin, crosslinked with carbodiimide or genepin; and the solvated polymer is a resorbable polyester, including polylactide, polyglycolide, or polycaprolactone or copolymers of these materials, including poly(lactide-/glycolide) acid (PLGA) or poly(lactide-co-ϵ-caprolactone) (PLCL). The compositions may be visible by ultrasound. The compositions may further comprise tissue scarring agents, fibrosis agents, fertilization inhibitors, contraceptive agents, tissue growth promoters, hormones, polymerization inhibitors, polymerization stabilizers, emulsifying agents, echogenic agents, contrast agents, viscosity-modifying materials, plasticizers, colorants or combinations thereof.

The cured compositions of the present invention swell less than 20%, and may be about 20% to about 100% substantially resorbed in a range of about 30 to about 365 days. Once resorbed the occlusion may be maintained by tissue ingrowth.

Compositions of the present invention may also comprise a liquid tissue adhesive and particles. The particles may be nano- or micro-particles comprising spheres of resorbable polymers. The particles may be from about 0.1 micrometer to about 1000 micrometers in diameter. The compositions may be viewable by ultrasound. The compositions may further comprise a curable carrier for the occlusive materials, a control release agent, tissue scarring agents, fibrosis agents, fertilization inhibitors, contraceptive agents, tissue growth promoters, hormones, polymerization inhibitors, polymerization stabilizers, emulsifying agents, echogenic agents, contrast agents, viscosity-modifying materials, plasticizers, colorants or combinations thereof.

The present invention comprises methods for contraception comprising providing a delivery system capable of delivering an effective amount of a composition comprising an occlusive material, wherein the delivery system comprises a delivery device comprising at least an introducer shaft for providing at least two catheters; two dual lumen balloon catheters; a composition comprising an occlusive material and means for providing the composition comprising an occlusive material into and through the catheters; delivering an effective amount of the composition comprising an occlusive material at or near the target location such that the material occludes the lumen of at least one fallopian tube; and occluding the fallopian tube with the composition comprising an occlusive material within the lumen of the conduit.

The present invention comprises devices, including contraceptive devices, comprising an introducer shaft for providing at least two catheters; two catheters, each comprising an end structure at the delivery end; a composition comprising an occlusive material, and means for providing the composition comprising an occlusive material into and through the catheters. The end structure may be a cup, nozzle, or a balloon. The devices may further comprise a delivery device stabilizer for holding the contraceptive device in place once positioned. The delivery device stabilizer may fit over or attach to the cervix or fit into or expand within the cervix to hold the device in position.

The present invention also comprises systems and methods for opening occluded conduits. A method comprises providing a delivery device comprising at least an introducer shaft for providing at least two catheters; two catheters, each comprising an end structure at the delivery end; and means for re-opening the conduit; and re-opening or opening the conduit. A device that may be used to open conduits comprises at least an introducer shaft for providing at least two catheters; at least one catheter, comprising a stationary device at one end; means for holding the delivery system in place upon positioning; and means for opening the conduit. Means for opening the conduit comprise device or members for providing shockwaves to shatter the occluding material, chemical means including solvents, biological means including enzymes, or mechanical means including stiff or cutting catheter ends to recanalize the lumen. The method may further comprise maintaining the opening of the conduit by providing a stent within the lumen of the conduit.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention describe in detail methods, delivery systems, and compositions to occlude the fallopian tubes of human, the present invention is not limited to these embodiments. There are numerous modifications or alterations that may suggest themselves to those skilled in the art for use of the methods, delivery systems, and compositions herein for the occlusion of a variety of conduits in both human and non-human mammals.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Implantable Material A

A solution of 25/75 poly lactide-co-ϵ-caprolactone (PLCL) was prepared 50% by weight in n-methyl-pyrrolidone (NMP) and sterilized. A mixture of 2-methoxypropyl cyanoacrylate (MPCA) with a biocompatible acid, in this case glacial acetic acid (AA), was prepared containing approximately 1 part MPCA and 1 part AA and sterilized. Implantable material A was prepared immediately prior to use by mixing 0.8 cc PLCL solution with 0.2 cc MPCA mixture until homogeneity of the mixture was achieved. The resultant mixture initially warms indicative of curing but remains adhesive to tissue and flowable through a 20G IV catheter for at least 15 min at room temperature in the absence of an aqueous environment. In contact with either water or animal tissue, the implantable material completes its curing quickly, forming a semi-solid material that is compressible and flakes relatively easily.

Example 2

Preparation of Implantable Material B

A solution of 50/50 poly lactide-co-glycolide (PLGA) was prepared 25% by weight in ethyl alcohol (EtOH) and sterilized. A mixture of butyl cyanoacrylate (BCA) with AA was prepared containing approximately 2 parts BCA and 1 part AA and sterilized. Implantable material B was prepared immediately prior to use by mixing 0.4 cc PLGA solution with 0.4 cc BCA mixture until homogeneity of the mixture was achieved. The resultant mixture initially warms indicative of curing but remains strongly adhesive to tissue and flowable through a 20G IV catheter for at least 15 min at room temperature in the absence of an aqueous environment. In contact with either water or animal tissue, the implantable material completes its curing quickly, forming a relatively incompressible semi-solid material that fractures on attempted bending.

Example 3

Preparation of Implantable Material C

Particles of 50/50 PLGA were prepared by dissolving PLGA in methylene chloride to create a 25% weight/volume solution, emulsifying in a 0.3% polyvinyl alcohol (PVA) solution, and further addition of PVA solution with 2% isopropyl alcohol to remove solvent. Particles were collected, lyophilized, and sterilized. Particles (0.25 g) were added to 0.75 g of a sterilized mixture containing 2 parts BCA and one part AA. The resulting particulate suspension was flowable at room temperature but cured on contact with water or animal tissue, forming a stiff, adherent material.

Example 4

Preparation of Implantable Material D

Particles of 50/50 PLGA were prepared as described in Example 3 with the addition of hydroquinone (0.5%) to the PVA emulsification, resulting in the entrapment of hydroquinone on the surface of the particles. The particles were collected, lyophilized, and sterilized. Particles (0.25 g) were added to 0.75 g of sterilized BCA. The particulate suspension remained flowable at room temperature with no indication of cyanoacrylate polymerization. The composition hardened on exposure to water or tissue, forming a stiff, adherent material.

Example 5

Study of 3 Implantable Materials in the Rabbit Fallopian Tube

Three candidate materials prepared similarly to the previous examples have been studied for their ability to create a mechanical occlusion and generate a tissue ingrowth response when placed into the fallopian tubes of rabbits. A fourth material, methyl cyanoacrylate (MCA), previously used to effect female sterilization in animals and humans but shown to have an unacceptable biocompatibility profile, was used as a control. Each of the test and control materials was placed into the fallopian tubes of three New Zealand white rabbits through an open procedure in which a 20G IV catheter was used as the delivery system. Materials were infused through the catheter into the cornual aspect of the right and left uterine body; finger pressure was used to prohibit backward flow of the material into the remainder of the uterus. Forward flow of the material was stopped once materials were seen within the cul-de-sac (i.e., peritoneal spill had occurred) or the full volume of material had been delivered. It was noted that, in comparison to the control material which cured very rapidly, sticking to the catheter, and with a high heat of curing, the test materials had a longer curing timeframe (within the time prior to closure but sufficiently long to remove the catheter without adhesion) and did not generate as much heat. Once both right and left tubes had been treated, the reproductive organs were repositioned within the pelvis, and the incision was closed. At 14 days, the animals were sacrificed. Dye infusion testing demonstrated that the fallopian tubes of all animals were blocked. One test material had generated an excessive amount of inflammation and adhesions and was ruled out. The remaining test materials and the control generated an appropriate tissue response, completely blocking the lumen of the fallopian tube with inflammatory cells and debris.

Example 6

Use of the Delivery System in Explanted Human Uteri

A prototype delivery system comparable to that shown in FIG. 1 was used to delivery dye and occlusive material to the fallopian tubes of three explanted human uteri obtained in accordance with the rules of the institution's Institutional Review Board. In each case, the explanted uterus was placed on an examination table in anatomic position, and the shaft of the introducer was placed transcervically until the tip reached the top of the uterine fundus as determined by tactile feel. Each of two balloon catheters was then advanced through the channel in the introducer until it was felt to lodge within the cornual aspect of the uterus. The balloons were inflated until resistance was felt. The uterus was then bivalved to allow for visualization of the device, which, in each case, was seen to be appropriately placed. One case represented a normal, multiparous uterus, while two cases demonstrated significant leiomyomatous pathology, indicating that the presence of fibroids outside the midline or the cornua does not interfere with the successful use of the delivery system. After successful placement was confirmed, a series of liquid injections through the catheters was conducted: first with saline to confirm patency, second with a hematoxylin dye to demonstrate that backflow into the uterine cavity did not occur, and finally with an occlusive material from the animal study in the previous example to demonstrate full functionality of the system in humans. In each case tested, dye demonstrated forward flow without leakage into the uterine cavity, and the material was successfully delivered.

Example 7

Occluding Compositions

| Component A | Component B | Additive(s) | Functionality of additive |
|---|---|---|---|
| 50% Gelatin-resorcinol | 50% Formaldehyde-glutaraldehyde | — | — |
| 50% Gelatin-resorcinol | 50% Formaldehyde-glutaraldehyde | Microbubbles of air | Ultrasound visibility |
| 50% Gelatin-resorcinol | 50% Formaldehyde-glutaraldehyde | Progesterone-estrogen - dissolved in component B | Inhibition of ovulation during maturation of blockage |
| 50% Gelatin-resorcinol | 50% Formaldehyde-glutaraldehyde | Tetracyline - dissolved in component B | Promotion of scarring or fibrosis |
| 50% Gelatin-resorcinol | 50% Formaldehyde-glutaraldehyde | bFGF, EGF - dissolved in component B | Induction of tissue ingrowth |
| 50% Gelatin-resorcinol | 50% Formaldehyde-glutaraldehyde | Gold particles suspended in component A | X-ray visibility |
| 50% Gelatin-resorcinol | 50% Formaldehyde-glutaraldehyde | Copper sulfate - dissolved or suspended in component A | Inhibition of ovulation and/or enhanced MRI visibility |
| 70% Fibrin glue | 30% poly-L-lactide dissolved 50% by weight in NMP | — | — |
| 70% Fibrin glue | 30% poly-L-lactide dissolved 50% by weight in NMP | Microbubbles of air | Ultrasound visibility |
| 70% Fibrin glue | 30% poly-L-lactide dissolved 50% by weight in NMP | Progesterone-estrogen - dissolved in component B | Inhibition of ovulation during maturation of blockage |
| 70% Fibrin glue | 30% poly-L-lactide dissolved 50% by weight in NMP | Tetracyline - dissolved in component B | Promotion of scarring or fibrosis |
| 70% Fibrin glue | 30% poly-L-lactide dissolved 50% by weight in NMP | bFGF, EGF - dissolved in component B | Induction of tissue ingrowth |
| 70% Fibrin glue | 30% poly-L-lactide dissolved 50% by weight in NMP | Gold particles suspended in component A | X-ray visibility |
| 70% Fibrin glue | 30% poly-L-lactide dissolved 50% by weight in NMP | Copper sulfate - dissolved or suspended in component A | Inhibition of ovulation and/or enhanced MRI visibility |
| 11% n-butyl cyanoacrylate | 89% poly-DL-lactide-co-glycolide dissolved 50% by weight in NMP | — | — |
| 11% n-butyl cyanoacrylate | 89% poly-DL-lactide-co-glycolide dissolved 50% by weight in NMP | Microbubbles of air | Ultrasound visibility |
| 10% n-butyl cyanoacrylate | 80% poly-DL-lactide-co-glycolide dissolved 50% by weight in NMP | 10% lactic acid, Microbubbles of air | Inhibition of polymerization, Ultrasound visibility |
| 11% n-butyl cyanoacrylate | 89% poly-DL-lactide-co-glycolide dissolved 50% by weight in NMP | Progesterone-estrogen - dissolved in component B | Inhibition of ovulation during maturation of blockage |
| 11% n-butyl cyanoacrylate | 89% poly-DL-lactide-co-glycolide dissolved 50% by weight in NMP | Tetracyline - dissolved in component B | Promotion of scarring or fibrosis |
| 11% n-butyl cyanoacrylate | 89% poly-DL-lactide-co-glycolide dissolved 50% by weight in NMP | bFGF, EGF - dissolved in component B | Induction of tissue ingrowth |
| 11% n-butyl cyanoacrylate | 89% poly-DL-lactide-co-glycolide dissolved 50% by weight in NMP | Gold particles suspended in component A | X-ray visibility |
| 11% n-butyl cyanoacrylate | 89% poly-DL-lactide-co-glycolide dissolved 50% by weight in NMP | Copper sulfate - dissolved or suspended in component A | Inhibition of ovulation and/or enhanced MRI visibility |
| 33% methoxypropyl cyanoacrylate | 67% poly-DL lactide-co-glycolide dissolved 50% by weight in NMP | — | — |
| 33% methoxypropyl cyanoacrylate | 67% poly-DL-lactide-co-glycolide dissolved 50% by weight in NMP | Microbubbles of air | Ultrasound visibility |
| 31% methoxypropyl cyanoacrylate | 62% poly-DL-lactide-co-glycolide dissolved 50% by weight in NMP | 7% lactic acid, Microbubbles of air | Inhibition of polymerization, Ultrasound visibility |
| 33% methoxypropyl cyanoacrylate | 67% poly-DL-lactide-co-glycolide dissolved 50% by weight in NMP | Progesterone-estrogen - dissolved in component B | Inhibition of ovulation during maturation of blockage |

-continued

| Component A | Component B | Additive(s) | Functionality of additive |
|---|---|---|---|
| 33% methoxypropyl cyanoacrylate | 67% poly-DL-lactide-co-glycolide dissolved 50% by weight in NMP | Tetracyline - dissolved in component B | Promotion of scarring or fibrosis |
| 33% methoxypropyl cyanoacrylate | 67% poly-DL-lactide-co-glycolide dissolved 50% by weight in NMP | bFGF, EGF - dissolved in component B | Induction of tissue ingrowth |
| 33% methoxypropyl cyanoacrylate | 67% poly-DL-lactide-co-glycolide dissolved 50% by weight in NMP | Gold particles suspended in component A | X-ray visibility |
| 33% methoxypropyl cyanoacrylate | 67% poly-DL-lactide-co-glycolide dissolved 50% by weight in NMP | Copper sulfate - dissolved or suspended in component A | Inhibition of ovulation and/or enhanced MRI visibility |
| 11% isohexyl cyanoacrylate | 89% poly-DL-lactide-co-ε-co caprolactone dissolved 50% by weight in ethyl alcohol | — | |
| 11% isohexyl cyanoacrylate | 89% poly-DL-lactide-co-ε-co-caprolactone dissolved 50% by weight in ethyl alcohol | Microbubbles of air | Ultrasound visibility |
| 10% isohexyl cyanoacrylate | 80% poly-DL-lactide-co-ε-co-caprolactone dissolved 50% by weight in ethyl alcohol | 10% acetic acid, Microbubbles of air | Inhibition of polymerization, Ultrasound visibility |
| 11% isohexyl cyanoacrylate | 89% poly-DL-lactide-co-ε-co-caprolactone dissolved 50% by weight in ethyl alcohol | Progesterone-estrogen - dissolved in component B | Inhibition of ovulation during maturation of blockage |
| 11% isohexyl cyanoacrylate | 89% poly-DL-lactide-co-ε-co-caprolactone dissolved 50% by weight in ethyl alcohol | Tetracyline - dissolved in component B | Promotion of scarring or fibrosis |
| 11% isohexyl cyanoacrylate | 89% poly-DL-lactide-co-ε-co-caprolactone dissolved 50% by weight in ethyl alcohol | bFGF, EGF - dissolved in component B | Induction of tissue ingrowth |
| 11% isohexyl cyanoacrylate | 89% poly-DL-lactide-co-ε-co-caprolactone dissolved 50% by weight in ethyl alcohol | Gold particles suspended in component A | X-ray visibility |
| 11% isohexyl cyanoacrylate | 89% poly-DL-lactide-co-ε-co-caprolactone dissolved 50% by weight in ethyl alcohol | Copper sulfate - dissolved or suspended in component A | Inhibition of ovulation and/or enhanced MRI visibility |
| 60% n-butyl cyanoacrylate | 40% poly-DL-lactide-co-glycolide microparticles emulsified in 4% polyvinyl alcohol | — | |
| 60% n-butyl cyanoacrylate | 40% poly-DL-lactide-co-glycolide microparticles emulsified in 4% polyvinyl alcohol | Microbubbles of air | Ultrasound visibility |
| 60% n-butyl cyanoacrylate | 30% poly-DL-lactide-co-glycolide microparticles emulsified in 4% polyvinyl alcohol | 10% lactic acid, Microbubbles of air | Inhibition of polymerization, Ultrasound visibility |
| 60% n-butyl cyanoacrylate | 40% poly-DL-lactide-co-glycolide microparticles emulsified in 4% polyvinyl alcohol | Progesterone-estrogen - dissolved in component A | Inhibition of ovulation during maturation of blockage |
| 60% n-butyl cyanoacrylate | 40% poly-DL-lactide-co-glycolide microparticles emulsified in 4% polyvinyl alcohol | Quinacrine - dissolved in component A | Promotion of scarring or fibrosis |
| 60% n-butyl cyanoacrylate | 40% poly-DL-lactide-co-glycolide microparticles emulsified in 4% polyvinylalcohol | BFGF, EGF - dissolved in component A | Induction of tissue ingrowth |
| 60% n-butyl cyanoacrylate | 40% poly-DL-lactide-co-glycolide microparticles emulsified in 4% polyvinylalcohol | Gold particles suspended in component A | X-ray visibility |
| 60% n-butyl cyanoacrylate | 40% poly-DL-lactide-co-glycolide microparticles emulsified in 4% polyvinylalcohol | Copper sulfate - dissolved or suspended in component A | Inhibition of ovulation and/or enhanced MRI visibility |

References

U.S. PATENT DOCUMENTS

| | | |
|---|---|---|
| 3,405,711 | 5,702,716 | 6,306,243 |
| 3,680,542 | 5,714,159 | 6,309,384 |
| 3,803,308 | 5,733,950 | 6,327,505 |
| 3,858,586 | 5,736,152 | 6,346,102 |
| Re 29,345 | 5,739,176 | 6,357,443 |
| Re 37,950 | 5,744,153 | 6,371,975 |
| 4,136,695 | 5,746,769 | 6,395,293 |
| 4,158,050 | 5,747,058 | 6,378,524 |
| 4,160,446 | 5,759,563 | 6,401,719 |
| 4,185,618 | 5,780,044 | 6,413,536 |
| 4,245,623 | 5,792,469 | 6,413,539 |
| 4,359,454 | 5,826,584 | 6,433,096 |
| 4,509,504 | 5,866,554 | 6,455,064 |
| 4,606,336 | 5,888,533 | 6,458,147 |
| 4,664,112 | 5,894,022 | 6,461,631 |
| 4,679,558 | 5,935,137 | 6,514,534 |
| 4,681,106 | 5,954,715 | 6,514,535 |
| 4,700,701 | 5,962,006 | 6,476,070 |
| 4,700,705 | 5,968,542 | 6,485,486 |
| 4,804,691 | 5,979,446 | 6,526,979 |
| 4,824,434 | 5,989,580 | 6,528,080 |
| 4,938,763 | 5,990,194 | 6,538,026 |
| 4,983,177 | 6,010,714 | 6,565,557 |
| 5,065,751 | 6,019,757 | 6,579,469 |
| 5,095,917 | 6,037,331 | 6,599,299 |
| 5,147,353 | 6,042,590 | 6,605,294 |
| 5,278,201 | 6,066,139 | 6,605,667 |
| 5,278,202 | 6,068,626 | 6,607,631 |
| 5,324,519 | 6,096,052 | 6,620,846 |
| 5,328,687 | 6,112,747 | 6,634,361 |
| 5,340,849 | 6,120,789 | 6,663,607 |
| 5,350,798 | 6,130,200 | 6,676,971 |
| 5,469,867 | 6,143,352 | 6,679,266 |
| 5,474,089 | 6,145,505 | 6,682,526 |
| 5,487,897 | 6,174,919 | 6,684,884 |
| 5,559,552 | 6,176,240 | 6,703,047 |
| 5,612,052 | 6,179,832 | 6,723,144 |
| 5,632,727 | 6,297,337 | 6,723,781 |
| 5,681,873 | 6,299,631 | 6,743,248 |

| FOREIGN PATENT DOCUMENTS | |
|---|---|
| WO 81/00701 | WO 99/07297 |
| WO 94/24944 | WO 99/47073 |
| WO 94/28803 | WO 00/44323 |
| WO 97/12569 | WO 00/24374 |
| WO 97/49345 | WO 01/37760 |
| WO 97/42987 | WO 02/39880 |
| WO 98/26737 | WO 03/070085 |
| WO 98/31308 | |

Other Publications
1. Abma J C, Chandra A, Mosher W D, et al. Fertility, family planning, and women's health: new data from the 1995 National Survey of Family Growth. *Vital Health Stat.* 1997; 23(19).
2. ACOG Practice Bulletin 46: Clinical management guidelines for obstetrician-gynecologists. *Obstetrics and Gynecology.* 2003; 102:647-658.
3. American Foundation for Urologic Disease. Facts about vasectomy safety.
4. Canavan T. Appropriate use of the intrauterine device. *American Academy of Family Physicians.* December 1998.
5. Clenney T, et al. Vasectomy Techniques. *American Academy of Family Physicians.* July 1999.
6. Fertility, Contraception and population policies. *United Nations, Population Division, Department of Economic and Social Affairs.* 25 Apr. 2003. ESA/P/WP.182.
7. Hendrix N, et al. Sterilization and its consequences. *Obstetrical and Gynecological Survey.* Vol 54(12), December 1999, p766.
8. Holt V L, et al. Oral contraceptives, tubal sterilization, and functional ovarian cyst risk. *Obstet Gynecol.* 2003; 102:252-258
9. Jamieson D J, et al. A comparison of women's regret after vasectomy versus tubal sterilization. *Obstetrics Gynecology.* 2002;99 1073-1079.
10. Snider S. The pill: 30 years of safety concerns. *U.S. Food and Drug Administration.* April 2001.
11. Viddya Medical News Service. Side effects of tubal ligation sterilizations. Vol 1, Issue 249.

What is claimed is:

1. A method for occluding at least one fallopian tube in a human or animal body, comprising,
   a) providing a delivery system that delivers an effective amount of an occlusive material composition the delivery system comprising a delivery device comprising an introducer shaft comprising a closed tip and defining at least one opening spaced from the closed tip for providing at least one catheter; at least one catheter comprising an end structure on a delivery end an occlusive material composition and means for providing the occlusive material composition into and through at least one catheter;
   b) positioning the closed tip of the introducer shaft at or near the fundus of a uterus;
   c) positioning the delivery end of at least one catheter at or near at least one uterine cornua such that the end structure is at or near a tubal ostium, wherein the end structure maintains the delivery end in the uterine cornua and aids in localized delivery of the occlusive material composition;
   d) delivering from the catheter to at least one tubal ostium and a portion of its fallopian tube an effective amount of the occlusive material composition to effect occlusion of at least one fallopian tube.

2. The method of claim 1, wherein two fallopian tubes are provided with an occlusive material without removal and re-introduction or substantial repositioning of the introducer shaft.

3. The method of claim 1, further comprising, e) reopening at least one fallopian tube.

4. The method of claim 1, wherein the occlusive material composition is mixed prior to delivery to the lumen.

5. The method of claim 1, wherein the occlusive material composition cures in situ to form a cured composition.

6. The method of claim 1 wherein the occlusive material composition is ultrasound visible.

7. The method of claim 6 wherein the ultrasound visible occlusive material composition comprises microbubbles of air or gas or microparticles of a material that entrap air or gas.

8. The method of claim 1, wherein the occlusive material composition comprises cyanoacrylate, polyacrylic acids, polyethylene glycols, modified polyethylene glycols, thrombin, collagen, collagen-based adhesives, fibrin, fibrin glue compositions, gelatin-resorcinol-formaldehyde-glutaraldehye (GRFG) glue, autologous blood in combination with collagen or thrombin, crosslinked albumin adhesives, modified glycosaminiglycans, poly(N-isopropylacrylamide)-based adhesives, alginates, or chitosan or gelatin, crosslinked with carbodiimide or genepin; a resorbable polyester of polylactide, polyglycolide, or polycaprolactone or copolymers of these materials, including poly(lactide-/glycolide) acid (PLGA) or poly(lactide-co-$\epsilon$-caprolactone) (PLCL).

9. The method of claim 5, wherein the cured composition swells less than 20%.

10. The method of claim 5, wherein the cured composition is about 20% to about 100% substantially resorbed in a range of about 30 to about 365 days.

11. The method of claim 1, wherein the occlusive material composition comprises particles.

12. The method of claim 11, wherein the particles are nano- or micro-particles comprising spheres of resorbable polymers.

13. The method of claim 11, wherein the particles are from about 0.1 micrometer to about 1000 micrometers in diameter.

14. The method of claim 8, wherein the occlusive material composition further comprises tissue scarring agents, fibrosis agents, fertilization inhibitors, contraceptive agents, tissue growth promoters, hormones, polymerization inhibitors, polymerization stabilizers, emulsifying agents, echogenic agents, contrast agents, viscosity-modifying materials, plasticizers, colorants or combinations thereof.

15. The method of claim 8, wherein the occlusive material_composition further comprises a curable carrier for the occlusive materials, a control release agent, tissue scarring agents, fibrosis agents, fertilization inhibitors, contraceptive agents, tissue growth promoters, hormones, polymerization inhibitors, polymerization stabilizers, emulsifying agents, echogenic agents, contrast agents, viscosity-modifying materials, plasticizers, colorants or combinations thereof.

16. A method for contraception, comprising,
   a) providing a delivery system that delivers an effective amount of an occlusive material composition, wherein the delivery system comprises a delivery device comprising an introducer shaft with a closed tip that provides at least one catheter; at least one dual lumen balloon catheter comprising a balloon end structure on a delivery end; an occlusive material composition and means for providing the occlusive material composition into and through at least one catheter;

b) positioning the closed tip of the introducer shaft at or near the fundus of a uterus;

c) positioning the delivery end of at least one catheter at or near at least one uterine cornua such that the end structure is at or near a tubal ostium, wherein the balloon end structure maintains the delivery end in the uterine cornua and aids in localized delivery of the occlusive material composition;

d) delivering from the catheter to at least one tubal ostium and a portion of its fallopian tube an effective amount of the occlusive material composition; and e) occluding the fallopian tube.

17. A method for occluding at least one fallopian tube in a mammal, comprising, a) providing a delivery system that delivers an effective amount of an occlusive material composition, the delivery system comprising a delivery device comprising at least a handle; an introducer shaft having a proximal end operatively connected to the handle and an opposed closed tip, the introducer shaft defining at least one catheter channel along the interior length of the introducer shaft and defining at least one respective catheter channel opening spaced proximally from the closed tip of the introducer shaft, wherein the at least one catheter channel is configured for providing a respective catheter; at least one catheter having a delivery end, wherein at least one catheter is configured to be received therein the at least one catheter channel of the introducer shaft; an occlusive material composition; and means for providing the occlusive material composition into and through the at least one catheter;

b) inserting the introducer shaft therethrough a cervix of the mammal until the closed tip contacts a uterine fundus of the mammal, and at least one catheter channel opening is directed toward a uterine cornua of the mammal;

c) moving at least one catheter therethrough at least one catheter channel until the delivery end of the catheter exits the catheter channel opening and the delivery end of at least one catheter is located within at least one uterine cornua and the end structure is at or near a tubal ostium, wherein the end structure maintains the delivery end in the uterine cornua and aids in localized delivery of the occlusive material composition; and d) delivering an effective amount of the occlusive material composition through and out the delivery end of at least one catheter so that a fallopian tube is occluded.

18. The method of claim 17, wherein the delivery system further comprises a delivery device stabilizer movably positioned thereon the introducer shaft, the method further comprising, after inserting the introducer shaft therethrough the cervix of the mammal, moving the delivery device stabilizer to a selected position along the introducer shaft to maintain the position of the closed tip on the uterine fundus.

19. The method of claim 17, further comprising, e) withdrawing at least one catheter therein the introducer shaft; and f) withdrawing the introducer shaft from the cervix of the mammal, thereby removing the delivery system from the mammal.

20. A method for delivering a fluid composition to at least one fallopian tube in a mammal, comprising, a) providing a delivery system that delivers an effective amount of a fluid composition the delivery system comprising a delivery device comprising at least a handle; an introducer shaft having a proximal end operatively connected to the handle and an opposed closed tip, the introducer shaft defining at least one catheter channel along the interior length of the introducer shaft and defining at least one respective catheter channel opening spaced proximally from the closed tip of the introducer shaft, wherein at least one catheter channel is configured for providing a respective catheter; at least one dual lumen balloon catheter having a delivery end and an end structure, wherein at least one catheter is configured to be received therein at least one a respective catheter channel of the introducer shaft; a fluid composition; and means for providing the fluid composition into and through the at least one catheter;

b) inserting the introducer shaft therethrough a cervix of the mammal until the closed tip contacts a uterine fundus of the mammal, wherein when the closed tip contacts the uterine fundus, at least one catheter channel opening is directed toward a uterine cornua of the mammal;

c) moving at least one catheter therethrough at least one catheter channel until the delivery end of at least one catheter exits the catheter channel opening and the delivery end of at least one catheter is located at or near at least one uterine cornua, wherein the end structure maintains the delivery end in the uterine cornua and aids in localized delivery of the fluid composition;

d) delivering from at least one catheter to at least one tubal ostium and a portion of its fallopian tube an effective amount of the fluid composition.

21. The method of claim 20, wherein the delivery system further comprises a delivery device stabilizer movably positioned thereon the introducer shaft, the method further comprising, after inserting the introducer shaft therethrough the cervix of the mammal, moving the delivery device stabilizer to a selected position along the introducer shaft to maintain the position of the closed tip on the uterine fundus.

22. A method for contraception of a mammal, comprising, a) providing a delivery system that delivers an effective amount of an occlusive material composition, the delivery system comprising a delivery device comprising at least a handle; an introducer shaft having a proximal end operatively connected to the handle and an opposed closed tip, the introducer shaft defining at least one catheter channel along the interior length of the introducer shaft and defining at least one respective catheter channel opening spaced proximally from the closed tip of the introducer shaft, wherein at least one catheter channel is configured for providing a catheter; at least one catheter having a delivery end and an end structure, wherein at least one catheter is configured to be received therein at least one catheter channel of the introducer shaft; an occlusive material composition; and means for providing the composition occlusive material into and through at least one catheter;

b) inserting the introducer shaft therethrough a cervix of a mammal until the closed tip contacts a uterine fundus of the mammal, wherein when the closed tip contacts the uterine fundus, at least one catheter channel opening is directed toward a uterine cornua of the mammal;

c) moving at least one catheter therethrough at least one catheter channel until the delivery end of at least one catheter exits the catheter channel opening and the delivery end of the at least one catheter is located at or near at least one uterine cornua and the end structure is at or near a tubal ostium, wherein the end structure maintains the delivery end in the uterine cornua and aids in localized delivery of the occlusive material composition;

d) delivering from the catheter to at least one tubal ostium and a portion of its fallopian tube an effective amount of the occlusive material composition; and e) occluding at least one fallopian tube.

23. The method of claim 22, wherein the delivery system further comprises a delivery device stabilizer movably positioned thereon the introducer shaft, the method further comprising, after inserting the introducer shaft therethrough the cervix of the mammal, moving the delivery device stabilizer to a selected position along the introducer shaft to maintain the position of the closed tip on the uterine fundus.

24. The method of claim 1, wherein the at least one opening comprises two openings, and wherein the at least one catheter comprises two catheters.

25. The method of claim 24, wherein each of the two openings provides a respective catheter of the two catheters.

26. The method of claim 1, wherein positioning the delivery end of at least one catheter comprises c1) positioning the delivery ends of two catheters, each respectively at or near a uterine cornua such that each catheter end structure is near a tubal ostium; and d1) delivering from each catheter an effective amount of the occlusive material composition to effect occlusion of two fallopian tubes.

27. The method of claim 1, wherein the end structure is a nozzle, cup or balloon.

28. The method of claim 17, wherein the end structure is a nozzle, cup or balloon.

29. The method of claim 20, wherein the end structure is a nozzle, cup or balloon.

30. The method of claim 22, wherein the end structure is a nozzle, cup or balloon.

* * * * *